United States Patent
Maina-Nock et al.

(10) Patent No.: US 10,449,260 B2
(45) Date of Patent: Oct. 22, 2019

(54) ENHANCED IN VIVO TARGETING OF RADIOLABELLED PEPTIDES WITH THE MEANS OF ENZYME INHIBITORS

(76) Inventors: Theodosia Maina-Nock, Athens (GR); Berthold Artur Nock, Athens (GR); Marion de Jong Hendriks, TN Vlaardingen (NL)

( * ) Notice: Subject to any disclaimer, the term of this patent is extended or adjusted under 35 U.S.C. 154(b) by 656 days.

(21) Appl. No.: 14/131,573

(22) PCT Filed: Jul. 6, 2012

(86) PCT No.: PCT/EP2012/063326
§ 371 (c)(1),
(2), (4) Date: Jun. 11, 2014

(87) PCT Pub. No.: WO2013/007660
PCT Pub. Date: Jan. 17, 2013

(65) Prior Publication Data
US 2015/0104381 A1    Apr. 16, 2015

(30) Foreign Application Priority Data

Jul. 8, 2011 (EP) ..................... 11173281

(51) Int. Cl.
| | | |
|---|---|---|
| A61K 51/00 | (2006.01) | |
| A61M 36/14 | (2006.01) | |
| A61K 51/08 | (2006.01) | |
| A61K 31/265 | (2006.01) | |
| A61K 31/7056 | (2006.01) | |
| A61K 45/06 | (2006.01) | |
| A61K 31/7028 | (2006.01) | |

(52) U.S. Cl.
CPC .......... *A61K 51/085* (2013.01); *A61K 31/265* (2013.01); *A61K 31/7028* (2013.01); *A61K 31/7056* (2013.01); *A61K 45/06* (2013.01); *A61K 51/08* (2013.01); *A61K 51/083* (2013.01); *A61K 51/086* (2013.01); *A61K 51/088* (2013.01)

(58) Field of Classification Search
CPC .... A61K 51/00; A61K 51/086; A61K 51/085; A61K 45/00; A61K 45/06; A61K 51/083; A61K 51/08; A61K 51/088; A61K 31/00; A61K 31/265; A61K 31/7028; A61K 31/7056; A61K 2123/00; A61K 51/0497; A61K 2300/00; C07K 7/06
USPC ....... 424/1.11, 1.65, 1.69, 9.1, 9.2; 530/300; 514/1, 1.1, 19.2, 19.3

See application file for complete search history.

(56) References Cited

U.S. PATENT DOCUMENTS

| | | | | |
|---|---|---|---|---|
| 5,200,426 A | * | 4/1993 | Hersh .................. | A61K 31/195 514/475 |
| 5,597,894 A | * | 1/1997 | Coy ..................... | C07K 14/655 530/311 |
| 5,601,801 A | | 2/1997 | Flanagan et al. | |
| 7,863,245 B2 | * | 1/2011 | Quay .................. | A61K 38/1709 514/5.2 |
| 2006/0211752 A1 | | 9/2006 | Kohn et al. | |
| 2008/0213172 A1 | | 9/2008 | Babich et al. | |
| 2009/0318330 A1 | | 12/2009 | De Jong et al. | |

OTHER PUBLICATIONS

Shaw et al, Biochimica et Biophysica Acta, General Subjects, 1987, 924, No. 1, pp. 167-174.*
Froeberg et al, Imaging, 2009, vol. 36, No. 8, pp. 1265-1272.*
Shaw et al, Biochimica et Biophysica Acta, vol. 924, pp. 167-174. (Year: 1987).*
Abd-Elgaliel et al., "Design, Sythesis and Biological Evaluation of a Radiolabelled Antagonist-Bombesin Analog as Targeting Vector", Bioconjuagate Cheimistry, Oct. 2008, pp. 2040-2048, vol. 19, No. 10.
Ananias, et al., "Nuclear Imaging of Prostate Cancer with Gastrin-Releasing-Peptide-Receptor Targeted Radiopharmaceuticals", Current Pharmaceutical Design, 2008, pp. 3033-3047, vol. 14, No. 28.
Blauenstein et al., "Improving the Tumor Uptake of 99mTc-Labeled Neuropeptides Using Stabilized Peptide Analogues", Cancer Biotherapy and Radiopharmaceuticals, Jan. 1, 2004, pp. 181-189, vol. 19, No. 2.
Cescato et al., "Bombesin Receptor Antagonists May Be Preferable to Agonists for Tumor Targeting", The Journal of Nuclear Medicine, Feb. 2008, pp. 318-326, vol. 49 No. 2.
De Visser, et al., "Stabilised $^{111}$In-labelled DTPA- and DOTA-Conjugated Neurotensin Analogues for Imagaing and Therapy of Exocrine Pancreatic Cancer", European Journal of Nuclear Medicine and Molecular Imaging, Aug. 2003, pp. 1134-1139, vol. 30, No. 8.
Donahue, et al., "Preparation fo a Protected Phosphoramidon Precursor Via an H-Phosphonate Coupling Strategy", Bioorganic & Medicinal Chemistry Letters, 2006, pp. 5602-5604, vol. 16.
Gabriel et al., "[99mTc]Demotensin VI: Biodistribution and Initial Clinical Results in Tumor Patients of a Pilot/Phase I Study", Cancer Biotherapy and Radiopharmaceuticals, 2011, pp. 557-563, vol. 26, No. 5.
Gotthardt et al., "Indication for different mechanisms of kidney uptake of radiolabeled peptides", Journal of Nuclear Medicine, Apr. 2007, pp. 596-601, vol. 48, No. 4.
Jaggi et al., "Mitigation of radiation nephropathy after initial alpha-particle irradiation of kidneys", International Journal of Radiation: Oncology Biology Physics, Apr. 1, 2006, pp. 1503-1512, vol. 64, No. 5.
Lagente et al., "Phosphoramidon potentiates the bronchoconstriction induced by inhaled bombesin in guinea pigs", Life Sciences, Jan. 1, 1993, pp. PL75-PL80, vol. 53, No. 5.

(Continued)

*Primary Examiner* — D. L. Jones
(74) *Attorney, Agent, or Firm* — Thompson Coburn LLP; William A. Holtz

(57) ABSTRACT

The present invention relates to a compound that inhibits the activity of a degrading enzyme for use in combination with a therapeutic or diagnostic compound, preferably a moiety conjugated peptide, in the diagnosis and/or treatment of a disease, in particular cancer, to enhance targeting of the therapeutic or diagnostic compound to the disease site.

6 Claims, 35 Drawing Sheets

(56) References Cited

OTHER PUBLICATIONS

Figure 1:
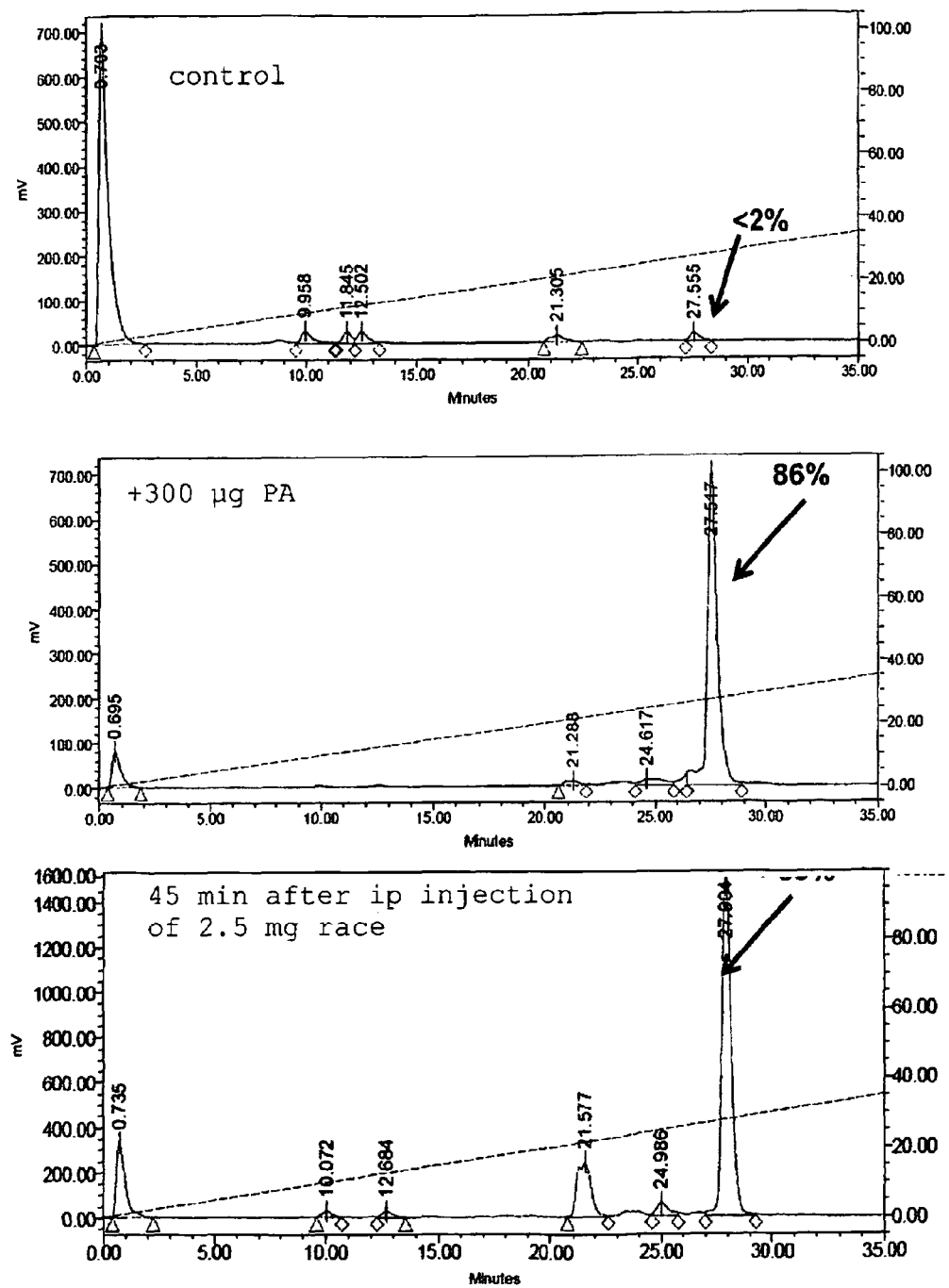

Lantry et al., "177Lu-AMBA: Synthesis and Characterization of a Selective 177Lu-Labeled GRP-R Agonist for Systemic Radiotherapy of Prostate Cancer", The Journal of Nuclear Medicine, Jul. 2006, pp. 1144-1152, vol. 47 No. 7.

Maes et al., "Novel 99mTc-Labeled Neurotensin Analogues with Optimized Biodistribution Properties", Journal of Medicinal Chemistry., Feb. 8, 2006, pp. 1833-1836, vol. 49, No. 5.

Maina et al., "[99mTc] Demotensin 5 and 6 in the NTS1-R-Targeted Imaging of Tumours: Synthesis and Preclinical Results", European Journal of Nuclear Medicine and Molecular Imaging, Jun. 27, 2007, pp. 1804-1814, vol. 34.

Maina et al., "Targeting Prostate Cancer with Radiolabelled Bombesins", Cancer Imaging, 2006, pp. 153-157, vol. 6.

Mansi et al., "Evaluation of a 1, 4, 7, 10-Tetraazacyclododecane-1, 4, 7, 10-Tetraacetic Acid-Conjugated Bombesin-Based Radioantagonist for the Labeling with Single-Photon Emission Computed Tomography, Positron Emission Tomography, and Therapeutic Radionuclides", Clinical Cancer Research, 2009, pp. 5240-5249, vol. 15 No. 16.

Nock et al., "[99mTc]Demobesin 1, A Novel Potent Bombesin Analogue for GRP Receptor-Targeted Tumour Imaging", European Journal fo Nuclear Medicine and Molecular Imgaing, Feb. 2003, pp. 247-258, vol. 30, No. 2.

Nock et al., "Potent Bombesin-like Peptides for GRP-Receptor Targeting of Tumors with 99mTc: A Preclinical Study", Journal of Medicinal Chemistry, 2005, pp. 100-110, vol. 48, No. 1.

Nock et al., "Toward stable N4-modified neurotensins for NTS1-receptor-targeted tumor imaging with 99mTC", Journal of Medicinal Chemistry, Jul. 27, 2006, pp. 4767-4776, vol. 49, No. 15.

Rolleman, "Kidney Protection During Peptide Receptor Radionuclide Therapy", Proesschriff ter verkrijging van de graad van doctor aan de Erasmus Universiteit Rotterdam, 2007, pp. 176PP and 106, paragraphs 1, 2, 4, Retrieved from the Internet, URL:http://repub.eur.nl/res/pub/10261/070614_Rollerman,%20Edgar%20Johannes.pdf.

Schroeder et al., "Gastrin-releasing peptide Receptor-based Targeting using Bombesin Analogues is Superior to Metabolism-based Targeting using Choline for in Vivo Imaging of Human Prostate Cancer Xenografts", European Journal of Nuclear Medicine and Molecular Imaging, 2011, pp. 1257-1266, vol. 38.

Smith et al., "Radiolabeled Peptide Conjugates for Targeting of the Bombesin Receptor Superfamily Subtypes", Nuclear Medicine and Biology, 2005, pp. 733-740, vol. 32.

Steinberg et al, "Blockade of neurotensin receptors by the antagonist SR 48692 partially prevents retrograde axonal transport of neurotensin in rat nigrostriatal system", Neuroscience Letters, Jan. 17, 1994, pp. 106-108, vol. 166, No. 1.

Wang et al., "Ligand binding, internalization, degradation and regulation by guanine nucleotides of bombesin eceptor subtypes: A comparative study", Biochemica Et Biophysica Acta. Molecular Cell Research, Jan. 17, 1993, pp. 232-242, vol. 1175, No. 2.

Wild et al, "Alpha-Versus Beta-Particle Radiopeptide Therapy in a Human Prostate Cancer Model (213Bi-DOTA-PESIN and 213Bi-AMBA Versus 177Lu-DOTA-PESIN)" Cancer Research, 2011, pp. 1009-1018, vol. 71.

Zhang et al., "Synthesis and Evaluation of Bombesin Derivatives on the Basis of Pan-Bombesin Peptides Labeled with Indium-111, Lutetium-177, and Yttrium-90 for Targeting Bombesin Receptor-Expressing Tumors", Cancer Research, Sep. 15, 2004, pp. 6707-6715, vol. 64.

* cited by examiner

ENHANCED IN VIVO TARGETING OF RADIOLABELLED PEPTIDES WITH THE MEANS OF ENZYME INHIBITORS

CROSS REFERENCE TO RELATED APPLICATIONS

This application is a U.S. National Phase application of PCT/EP2012/063326, filed on Jul. 6, 2012, claiming the benefit of European patent application EP-11173281.4, filed Jul. 8, 2011, both of which are incorporated herein by reference in their entireties.

FIELD OF THE INVENTION

The present invention relates to increasing the uptake at the site(s) of disease of diagnostic or therapeutic site-specific vectors, in particular radiolabeled peptide ligands, in the diagnosis and/or treatment of disease, especially cancer, by use of compounds inhibiting enzymes that degrade such vectors.

BACKGROUND OF THE INVENTION

Disease-sites, like cancer cells, (over)express "fingerprint" biomolecules, such as antigens or receptors, which may serve as recognition sites for a wide range of circulating vectors, such as antibodies, peptide-hormones, growth factors etc. One approach to diagnose and identify disease-sites is to exploit such interaction and to use a suitably modified vector, such as a peptide analog labeled with a diagnostic radionuclide, which will specifically accumulate on the disease-site(s) after administration to the patient. The tumor and metastases are then localized by imaging the site(s) where the radioactive decay occurs using an external imaging device.

A similar rationale is followed in targeted therapy, whereby the vector will again serve as the vehicle which will deliver a cytotoxic load, such as a therapeutic radiometal, specifically to the disease-sites, e.g. the tumor and metastases. The therapeutic radiolabel will then decay on the disease site, releasing particle radiation to kill or to reduce the growth of the tumor.

The efficacy of targeted diagnosis and treatment is often compromised by degradation of the administered site-specific drug by endogenous enzymes. Enzymatic breakdown may occur in the blood stream immediately after entry into circulation and until the drug reaches the target. Metabolic attack may be operated during transit by enzymes circulating in the blood solute, but most importantly, by enzymes anchored on the membrane of blood cells, vasculature walls and several tissues of the human body (liver, kidneys and gastrointestinal tract) including tumor tissue. These enzymes will greatly affect drug delivery. Furthermore, the micromilieu around the target, as for example the peritumoral environment (stroma cells, local (neo)vasculature and extracellular matrix), is another potential degradation site for diagnostic and therapeutic drugs, likely to affect not only accumulation but also retention at the target.

It has long been established, that the action of many endogenous substances, such as peptide-hormones, is regulated by enzymes, both in normal conditions and during cancer onset and propagation. Thus, an "intimate" relationship seems to exist for example between G protein coupled receptors (GPCRs), their peptide-ligands and related enzymes that are e.g. present in the bloodstream, in the extracellular matrix or on the cell membrane controlling the action of these ligands.

It is well documented that the proteolytic action of exopeptidases is one of the major degradation pathway for peptides. In order to escape attack of exopeptidases, chemical modifications of peptide termini have often been attempted. This approach is relatively simple, widely pursued and usually leads to more stable peptides of preserved biological activity. Consequently, N-terminal protection against aminopeptidases, such as acetylation or methylation, has been commonly applied to prolong the biological half-life of many peptide ligands.

It is interesting to note, that most peptide ligands conjugated to diagnostic or therapeutic moieties, such as (radio)metallated peptide ligands designed for molecular imaging or targeted therapy applications, are most often modified at the N-terminus. In general, a bifunctional chelator is covalently coupled via a carboxy functionality to the N-terminal amine of the peptide-ligand under formation of a peptide bond. While the original objective of this approach had been to introduce the metal chelate (or another medically relevant moiety), at a position as remote as possible from the receptor-recognition site to avoid interference during binding, it has inadvertently led to N-terminus capping. It is reasonable to assume that such radiometallated (or similarly conjugated) peptide ligands will therefore follow a different metabolic route than their free N-terminus counterparts and will be accordingly processed by enzymes other than aminopeptidases.

In view of the above, analogs of native receptor ligands, such as peptide-conjugates, in particular radiolabeled peptides, are expected to show sub-optimal targeting if not sufficiently modified to endure rapid enzymatic attack in the biological milieu. And in fact, this is most often observed during evaluation of many new (radio)peptide analogs. By studying the ex vivo blood of mice after administration of many radiometallated peptide ligands comprising somatostatin, gastrin, neurotensin and bombesin-like derivatives by HPLC the inventors have observed that most of these analogs were degraded to a certain extent within 5 min in vivo despite the metal-chelate coupled at their N-terminus. This finding is consistent with the inventors' assumption that proteolytic enzyme(s) other than aminopeptidases are involved in the rapid in vivo degradation of these classes of such radiolabeled peptide-conjugates.

In order to overcome problems imposed by the insufficient metabolic stability of peptide-conjugates, e.g. radiolabeled peptides, such as sub-optimal targeting and poor pharmacokinetics, painstaking research and expensive resources have been invested worldwide for the development of stabilized peptide-vectors. However, modifications undertaken to metabolically stabilize native lead-structures have often led to bioconjugates of poor interaction capacity to their cognate receptors and/or to compounds of undesirable pharmacological profile and/or sub-optimal pharmacokinetics.

It is therefore the object of the present invention to provide the means to enhance delivery of diagnostic and therapeutic agents, in particular of non- or partially stabilized peptide conjugates, optionally radiolabeled, to disease-sites.

SUMMARY OF THE INVENTION

In the research that led to the invention a totally different strategy was developed, namely the combined administration of a therapeutic or diagnostic compound with one or more other compounds. More specifically, it was found according to the invention that co-administration of compound(s) that inhibit the activity of certain enzyme(s) along with a therapeutic or diagnostic compound, in particular a peptide-conjugate preferably radiolabeled, or a peptide-radioligand, significantly enhances in vivo targeting. In this way, the invention allows to fully exploit the targeting capacity of potent but rapidly biodegradable therapeutic and diagnostic peptide-conjugates, such as radiolabeled peptide-conjugates. This fact is particularly relevant for the effective application of native peptide-ligand motifs for conjugation to suitable diagnostic and/or therapeutic moieties, such as to radiometal-chelates. These have been evolutionarily optimized to most efficiently interact with their cognate receptors, but their application in medicine has been excluded so far due to their rapid in vivo degradation.

A most surprising finding of the present invention is that the co-administration even of an inhibitor against a single enzyme—for example phosphoramidon (PA), a highly potent NEP (neutral endopeptidase) inhibitor—was not only effective to metabolically stabilize, or else to "protect", a wide range of radiolabeled neuropeptide-ligands in vivo, but most importantly, to provoke a dramatic increase of radio-ligand accumulation at the target. An unexpected prominent enhancement of in vivo stability was evidenced by analysis of ex vivo blood by HPLC 5 min after co-administration of phosphoramidon (PA) along with a wide range of different classes of radiolabeled biodegradable peptide-conjugates derived from somatostatin, gastrin, neurotensin, bombesin, neuromedin C and GRPR-antagonists.

Most importantly, this prolongation of in vivo half life translated into a marked increase of radiopeptide uptake at the target sites.

The present invention thus relates to a compound or a combination of compounds that inhibit(s) the activity of one or more degrading enzymes for use in combination with a therapeutic or diagnostic compound, preferably a moiety conjugated peptide, in the diagnosis and/or treatment of a disease, in particular cancer and/or infections.

The degrading enzyme(s) is (are) suitably a hydrolase, in particular a peptidase, such as a vasopeptidase or endopeptidase, in particular a neutral endopeptidase (NEP), angiotensin converting enzyme (ACE) or an esterase.

The therapeutic or diagnostic compound can be any compound that is used for treatment or diagnosis of the human or animal body, but is preferably a peptide-conjugate, in particular a peptide receptor ligand coupled to a suitable moiety and can be optionally radiolabeled for diagnostic imaging (PET, SPECT) and radionuclide therapy, or be labeled for optical imaging, with for example fluorescent molecules, or be labeled for MRI, or coupled to an anticancer drug.

Therapeutic and diagnostic compounds, or peptide ligand conjugates, that benefit most from this invention are metabolically non-stabilized compounds that are rapidly degraded in the human or animal body. Examples of such compounds are conjugates of somatostatins, in particular somatostatin-14 and its analogs, of CCK2/gastrin-R ligands, such as CCKs, gastrins, minigastrins and their analogs, in particular minigastrin(10-17), of neurotensin receptor ligands, in particular neurotensin subtype 1 receptors, such as neurotensin and its analogs, demotensins, of gastrin releasing peptide receptor (GRPR) ligands, in particular bombesin and its analogs, in particular demobesin 4 and demobesin 1, pansarbesin 1, of neuromedin C (NMC) and its analogs, in particular SAR-NCs such as SAR-NC1 and SAR-NC6, or the JMV compounds, in particular compound JMV4168. Bombesin analogs labeled with diagnostic and therapeutic radionuclides are for example disclosed in Maina T et al, 2006; Smith C J et al, 2005; Lantry L E et al, 2006; Zhang H et al, 2004; Nock B et al, 2005; Schroeder R P et al, 2011; Ananias H J et al, 2008; Wild D et al, 2011.

All these compounds can be labeled with a (radioactive) label for use in diagnosis/imaging or therapy. Suitable labels are Tc, In, Ga, Cu, F, Lu, Y, Bi, Ac, and other radionuclide isotopes. Preferably, the radionuclide is selected from the group comprising $^{111}$In, $^{99m}$Tc, $^{94m}$Tc, $^{67}$Ga, $^{66}$Ga, $^{68}$Ga, $^{52}$Fe, $^{69}$Er, $^{72}$As, $^{97}$Ru, $^{203}$Pb, $^{62}$Cu, $^{64}$Cu, $^{67}$Cu, $^{186}$Re, $^{188}$Re, $^{86}$Y, $^{90}$Y, $^{51}$Cr, $^{52m}$Mn, $^{157}$Gd, $^{177}$Lu, $^{161}$Tb, $^{169}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{177m}$Sn, $^{213}$Bi, $^{142}$Pr, $^{143}$Pr, $^{198}$Au, $^{199}$Au, $^{18}$F, $^{123}$I, $^{124}$I, $^{131}$I, $^{75}$Br, $^{76}$Br, $^{77}$Br, and $^{82}$Br, amongst others.

The enzyme inhibitor can be any inhibitor and is in particular selected from NEP (neutral endopeptidase) inhibitors, ACE (angiotensin-converting enzymes) inhibitors, ECE (endothelin converting enzyme) inhibitors, esterase inhibitors, and combinations thereof, as well as dual or triple inhibitors.

An enzyme inhibitor of a certain enzyme can be used alone or in combination with other inhibitors, in inhibitor mixtures or cocktails. Also dual or triple action inhibitors that inhibit more than one enzyme can be used.

NEP inhibitors are for example phosphoramidon (PA), racecadotril (race) and others known to the person skilled in the art.

ACE inhibitors are for example lisinopril (Lis), captopril and others known to the person skilled in the art.

In certain embodiments of the inventions, a compound that inhibits the activity of a degrading enzyme is use in combination with a therapeutic or diagnostic compound in the diagnosis and/or treatment of a disease to enhance targeting of the therapeutic or diagnostic compound to the disease site. In particular, the disease may be cancer and/or infections. In certain embodiments, the degrading enzyme is a hydrolase selected from peptidases, esterases. In certain embodiments, the enzyme is a neutral endopeptidase. In certain embodiments, the enzyme is angiotensin converting enzyme. In certain embodiments, the therapeutic or diagnostic compound is selected from receptor ligand-conjugates, in particular peptides coupled to metal chelators or to prosthetic groups, more in particular radioactively labeled peptides. Preferably, the present therapeutic or diagnostic compound is a moiety conjugated peptide. In certain embodiments, the radioactively labeled peptide is not completely stabilized. In certain embodiments, the peptide, is an antagonist. In certain embodiments, the peptide is an agonist. In certain embodiments, the compound is a peptide-conjugate and the peptide-part is a somatostatin, in particular somatostatin-14 and its analogs, CCK2R-receptor ligands, such as CCKs, gastrins, minigastrins and their analogs, in particular minigastrin(10-17), neurotensin receptor ligands, in particular neurotensin subtype 1 receptors, such as neurotensin and its analogs, demotensins and its analogs, in particular demotensin 1 or 6, gastrin releasing peptide receptor (GRPR) ligands, in particular bombesin and its analogs, in particular $^{99m}$Tc-demobesin 4 and $^{99m}$Tc-demobesin 1, neuromedin C (NMC) and its analogs, in particular $^{99m}$Tc-SAR-NCs such as $^{99m}$Tc-SAR-NC1 and $^{99m}$Tc-SAR-NC6, or universal bombesin ligands, in particular, $^{111}$In-pansarbesin 1, or the JMV compounds, in particular compound $^{111}$In/$^{177}$Lu/$^{68}$Ga-JMV4168, neuropeptide substance P such as SP-1, SP-2, melanocyte stimulating hormone (MSH), chemotactic peptide (CTP) or combinations thereof. In certain embodiments, the compound is a NEP inhibitor, in particular phosphoramidon or racecadotril; an ACE inhibitor, in particular lisinopril or captopril; an ECE inhibitor, or an esterase inhibitor.

In certain embodiments, compounds that are used in combination with a diagnostic or therapeutic vector in the diagnosis or treatment of a disease such as cancer increase the uptake of the vector at the disease site(s) by inhibiting the activity of degrading enzymes.

Certain embodiments of the invention are drawn to a method of treating and/or diagnosing a disease comprising co-administration of a therapeutic or diagnostic compound with one or more compounds that inhibit the activity of one or more hydrolase wherein the therapeutic or diagnostic compound comprises a peptide-ligand conjugate. In certain embodiments, the hydrolase is a peptidase or an esterase. The advantage of such a method is that the in vivo targeting of the therapeutic or diagnostic compound is enhanced as compared to in vivo targeting of the therapeutic or diagnostic compound in an absence of said compound(s) that inhibit the activity of said hydrolase. In certain embodiments, the peptide-ligand conjugate is a native peptide-ligand conjugate. In certain embodiments of methods of the invention, the therapeutic or diagnostic compound is a peptide-radioligand. In certain embodiments, it is labeled with a fluorescent molecule for optical imaging. In certain embodiments, the therapeutic or diagnostic compound is a radiolabeled biodegradable peptide-conjugate derived from the group consisting of somatostatin, gastrin, neurotensin, bombesin, neuromedin C, and a gastrin releasing peptide receptor-antagonist, the neuropeptide substance P such as SP-1, SP-2, melanocyte stimulating hormone (MSH), and chemotactic peptide (CTP).

In certain embodiments of methods of the invention the one or more compounds that inhibit the activity of one or more hydrolases is selected from the group consisting of neutral endopeptidase inhibitors, angiotensin-converting enzyme inhibitors, endothelin converting enzyme inhibitors, esterase inhibitors, and combinations thereof. In certain embodiments, the one or more compounds that inhibit the activity of a hydrolase is a neutral endopeptidase inhibitor. Representative examples of neutral endopeptidase inhibitors include phosphoramidon or racecadotril. In certain embodiments, the one or more compounds that inhibit the activity of a hydrolase is an angiotensin-converting enzyme inhibitor.

In certain embodiments of methods of the invention, the peptide-radioligand is a radiometallated or a radiohalogenated via a prosthetic group peptide. In certain embodiments, the peptide-radioligand comprises a radionuclide metal selected from the group consisting of $^{133m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{123}$I, $^{124}$I, $^{131}$I, $^{75}$Br, $^{76}$Br, $^{77}$B $^{82}$Br, $^{153}$Sm, $^{161}$Tb, $^{90}$Y, $^{177}$Lu, and other radionuclide metals useful in radiotherapy and/or imaging.

In certain embodiments of methods of the invention, the co-administration of the therapeutic or diagnostic compound and the one or more compounds that inhibit the activity of a hydrolase comprises:
(i) administering the therapeutic or diagnostic compound at the same time as the one or more compounds that inhibit the activity of one or more hydrolases;
(ii) first administering the therapeutic or diagnostic compound, followed by administering the one or more compounds that inhibit the activity of one or more hydrolases; or
(iii) first administering the one or more compounds that inhibit the activity of one or more hydrolases, followed administering the therapeutic or diagnostic compound.

In certain embodiments of method of the invention, the combination of a therapeutic or diagnostic compound and one or more compounds that inhibit the activity of one or more hydrolases is selected from the group of combinations consisting of: [(X-DOTA)Ala$^1$]SS14 or [(X-DOTA)Ala$^1$, DTrp$^8$]SS14 with a neutral endopeptidase inhibitor; X-DOTA-MG11 with a neutral endopeptidase inhibitor; X-demotensin 6 or X-demotensin 1 with a neutral endopeptidase inhibitor; X-demotensin 1 with a neutral endopeptidase inhibitor and/or an ACE inhibitor; X-SAR-NC1 or X-SAR-NC6 with a neutral endopeptidase inhibitor; X-Demobesin 4 or X-Demobesin 1 with a neutral endopeptidase inhibitor; X-Pansarbesin 1 with a NEP inhibitor; and X-JMV4168 with a neutral endopeptidase inhibitor, wherein X is a radionuclide useful for radiotherapy or imaging. In certain embodiments, the combination of a therapeutic or diagnostic compound and one or more compounds that inhibit the activity of one or more hydrolases is selected from the group of combinations consisting of: [($^{111}$In-DOTA)Ala$^1$]SS14 or [($^{111}$In-DOTA)Ala$^1$, DTrp$^8$]SS14 with a neutral endopeptidase inhibitor; $^{111}$In-DOTA-MG11 with a neutral endopeptidase inhibitor; $^{99m}$Tc-demotensin 6 or $^{99m}$Tc-demotensin 1 with a neutral endopeptidase inhibitor; $^{99m}$Tc-demotensin 1 with a neutral endopeptidase inhibitor and/or an ACE inhibitor; $^{99m}$Tc-SAR-NC1 or $^{99m}$Tc-SAR-NC6 with a neutral endopeptidase inhibitor; $^{99m}$Tc-Demobesin 4 or $^{99m}$Tc-Demobesin 1 with a neutral endopeptidase inhibitor; X-Pansarbesin 1 with a NEP inhibitor; and $^{111}$In-JMV4168 with a neutral endopeptidase inhibitor.

According to a further aspect, the present invention relates to compositions comprising a therapeutic or diagnostic compound that comprises a peptide-ligand, preferably a moiety conjugated peptide, and one or more compounds that inhibit the activity of one or more hydrolases. In certain embodiments, the hydrolase is a peptidase or an esterase. The advantage of such compositions is that administration of the composition enhances in vivo targeting of the therapeutic or diagnostic compound as compared to administration of just the therapeutic or diagnostic compound alone. In certain embodiments, the peptide-ligand is a native peptide-ligand. In certain embodiments, the peptide-ligand has an N-terminal modification.

In certain embodiments of a composition of the invention, the therapeutic or diagnostic compound is a peptide-radioligand. In certain embodiments, it is labeled with a fluorescent molecule for optical imaging. In certain embodiments, the therapeutic or diagnostic compound is a radiolabeled biodegradable peptide-conjugate derived from the group consisting of somatostatin, gastrin, neurotensin, bombesin, neuromedin C, and a gastrin releasing peptide receptor (GRPR)-antagonist.

In certain embodiments of a composition of the invention, the one or more compounds that inhibit the activity of a hydrolase is selected from the group consisting of neutral endopeptidase inhibitors, angiotensin-converting enzyme inhibitors, endothelin converting enzyme inhibitors, esterase inhibitors, and combinations thereof. In certain embodiments, the one or more compounds that inhibit the activity of hydrolase is a neutral endopeptidase inhibitor. Representative examples of neutral endopeptidase inhibitors include phosphoramidon or racecadotril. In certain embodiments, the one or more compounds that inhibit the activity of a hydrolase is an angiotensin-converting enzyme inhibitor.

In certain embodiments of a composition of the invention, the peptide-radioligand is an N-terminal radiometallated peptide. In certain embodiments, the peptide-radioligand, or moiety conjugated peptide, comprises a radionuclide metal selected from the group comprising $^{111}$In, $^{99m}$Tc, $^{94m}$Tc, $^{67}$Ga, $^{66}$Ga, $^{68}$Ga, $^{52}$Fe, $^{69}$Er, $^{72}$As, $^{97}$Ru, $^{203}$Pb, $^{62}$Cu, $^{64}$Cu, $^{67}$Cu, $^{186}$Re, $^{188}$Re, $^{86}$Y $^{90}$Y, $^{51}$Cr, $^{52m}$Mn, $^{157}$Gd, $^{177}$Lu, $^{161}$Tb, $^{169}$Yb, $^{175}$Yb, $^{105}$Rh, $^{166}$Dy, $^{166}$Ho, $^{153}$Sm, $^{149}$Pm, $^{151}$Pm, $^{172}$Tm, $^{121}$Sn, $^{177m}$Sn, $^{213}$Bi, $^{142}$Pr, $^{143}$Pr, $^{198}$Au, $^{199}$Au, $^{18}$F, $^{123}$I, $^{124}$I, $^{131}$I, $^{75}$Br, $^{76}$Br, $^{77}$Br, and $^{82}$Br, and other radionuclide metals useful in radiotherapy and/or imaging.

In certain embodiments of a composition of the invention, the composition comprises a combination selected from the group of combinations consisting of: [(X-DOTA)Ala1]SS-14 or [(X-DOTA)Ala1, DTrp8]SS-14 with a neutral endopeptidase inhibitor; X-DOTA-MG11 with a neutral endopeptidase inhibitor; X-demotensin 6 or X-demotensin 1 with a neutral endopeptidase inhibitor; X-demotensin 1 with a neutral endopeptidase inhibitor and/or lisinopril; X-SAR-NC1 or X-SAR-NC6 with a neutral endopeptidase inhibitor; X-Demobesin 4 or X-Demobesin 1 with a neutral endopeptidase inhibitor; and X-JMV4168 with a neutral endopeptidase inhibitor, wherein X is a radionuclide useful for radiotherapy or imaging.

In certain embodiments, the composition comprises a combination selected from the group of combinations consisting of: [($^{111}$In-DOTA)Ala1]SS-14 or [($^{111}$In-DOTA)Ala1, DTrp8]SS-14 with a neutral endopeptidase inhibitor; $^{111}$In-DOTA-MG11 with a neutral endopeptidase inhibitor; $^{99m}$Tc-demotensin 6 or $^{99m}$Tc-demotensin 1 with a neutral endopeptidase inhibitor; $^{99m}$Tc-demotensin 1 with a neutral endopeptidase inhibitor and/or lisinopril; $^{99m}$Tc-SAR-NC1 or $^{99m}$Tc-SAR-NC6 with a neutral endopeptidase inhibitor; $^{99m}$Tc-Demobesin 4 or $^{99m}$Tc-Demobesin 1 with a neutral endopeptidase inhibitor; and $^{111}$In-JMV4168 with a neutral endopeptidase inhibitor.

DETAILED DESCRIPTION OF THE INVENTION

The most surprising finding of the invention is the unexpected prominent role for mainly two vasopeptidases, and in particular of neutral endopeptidase (NEP, EC 3.4.24.11, or neprilysin, or CD10) and angiotensin converting enzyme, ACE, EC 3.4.15.1) in the in vivo processing of a great number of peptides conjugated to diagnostic or therapeutic moieties, in particular radiopeptides. In particular, the role of NEP in the processing of radiopeptides is consistent with its ubiquitous and abundant presence in the body. The significance of NEP involvement in the catabolism of all these classes of radiopeptide-ligands has not been adequately elucidated up to now.

It is an outstanding result of this invention, that the inhibition of NEP is elegantly exploited to enhance the in vivo stability and in vivo targeting of a wide range of biodegradable radiopeptide-ligands by administration of NEP inhibitor(s). As NEP plays a central role for many peptides' in vivo catabolism, then a NEP-inhibitor provides a common solution for all these peptides' instability. In a few cases where ACE is also involved the use of a dual NEP/ACE inhibitor or a cocktail of a NEP and an ACE inhibitor can synergistically provoke a more complete affect.

Another unexpected finding of this invention is that in many cases administration of phosphoramidon (PA) (or other enzyme inhibitor(s)) with the peptide radioligand resulted in markedly enhancing tumor values without, however, increasing background radioactivity. This is particularly important for renal and liver uptake values which in certain cases remained surprisingly unaffected after prolonging the biological half life of radiopeptides by administration of enzyme inhibitor(s), such as phosphoramidon (PA). As a result, unprecedented tumor-to-non-target ratios have been achieved and new promising opportunities for targeted radionuclide therapy have become accessible.

In addition, it was found that the pharmacokinetics of the combination of the peptide plus the inhibitor or inhibitor combination is most often superior in comparison to the use of stabilized peptides.

Another aspect of the central role of NEP in the metabolic fate of many radiopeptides resides on the expression and physiological role of NEP in the microenvironment, but also on the cancer cell membrane, of many human tumors, such as prostate, breast and colon cancers. Consequently, co-administration of a NEP-inhibitor will prolong the half-life of radiopeptides not only in the blood stream but also in the immediate vicinity of cancer cells. This strategy is particularly beneficial in prolonging the retention of non-internalizing radiolabeled GRPR- or other peptide-receptor-antagonists which remain bound on the surface of cancer cells and are thus longer exposed to extracellular peritumoral enzymes than fast internalizing radiolabeled agonists.

The pharmaceutical industry has been intensively engaged in the development of a wide range of vasopeptidase selective, single, dual and triple acting inhibitors (for NEP, ACE and/or ECE) as new therapeutic tools. These peptidases are involved in health and disease via modulation of many bioactive peptides, such enkephalin, bradykinin, substance P, endothelin, atrial natriuretic peptide and many others. Racecadotril, also known as acetorphan, is a prodrug releasing the active compound thiorphan as a racemic mixture. Thiorphan is an antidiarrheal drug, which acts as a potent NEP inhibitor ($K_i$ 1.7 nM (R-thiorphan) and 2.2 nM (S-thiorphan)). Furthermore, racecadotril can also inhibit ACE, but with a lower potency ($K_i$ 4800 nM (R-thiorphan) and 110 nM (S-thiorphan)).

Another suitable peptidase inhibitor for use in the invention is phosphoramidon (PA). Phosphoramidon is a known potent ($IC_{50}$ 34 nM) and reversible competitive inhibitor of NEP. Phosphoramidon inhibits also endothelin converting enzyme (ECE, 3.4.24.71) with moderate potency ($IC_{50}$ 3.5 μM) and with low potency angiotensin converting enzyme (ACE, 3.4.15.1) ($IC_{50}$ 78 μM). It was first isolated from cultures of Streptomyces tanashiensis (Umezawa S et al, 1972), but methods for its convenient synthesis have recently become available (Donahue M G et al, 2006).

The effects of phosphoramidon (PA) injection together with radiopeptides, representatives of somatostatin, gastrin, bombesin, neuromedin C, bombesin, neurotensin and GRPR-antagonists in prolonging in vivo half-life and enhancing tumor targeting will be presented below. Phosphoramidon was found to be equally effective when administered intraperitonealy (ip) 40-60 min prior to radioligand injection as well. Analogous effects were observed by intraperitoneal (ip) injection of a suspension of 2.5 mg racecadotril (in DMSO/water v/v 5/95) 40-60 min prior to radioligand injection.

Lisinopril (Lis) is a potent ACE inhibitor ($K_i$=0.1 nM) that can be used according to the invention. It was derived by research efforts initiated by studying the venom of a Brazilian pit viper (Bothrops jararaca). Lisinopril is historically the third ACE inhibitor after captopril and enalapril and is in fact the lysine analog of the latter. It is an approved drug primarily applied in the treatment of hypertension and congestive heart failure (Prinivil®; Zestril®).

The co-administration of the enzyme inhibitor and therapeutic or diagnostic compound, such as a radioactively labeled peptide, can be simultaneous or subsequent. In one embodiment the therapeutic or diagnostic compound is administered at the same time as the inhibitor. In another embodiment, the inhibitor is administered before the therapeutic or diagnostic compound. In still a further embodiment the therapeutic or diagnostic compound is administered first followed by the inhibitor. In the latter situation, the administration of the inhibitor follows preferably immediately after administration of the compound. In a further embodiment, it is possible to load or saturate the patient with the inhibitor prior to administration of the therapeutic or diagnostic compound for example by repeated oral administration of the inhibitor, for example followed by a bolus injection of the therapeutic or diagnostic compound.

The inhibitor and the therapeutic or diagnostic compound can be administered in various ways, such as per os, by inhalation, intranasal, intramuscularly, subcutaneously, intravenously, intraperitoneally or by infusion. It is not necessary to use the same administration route for both the inhibitor and the therapeutic or diagnostic compound. In the context of this invention the inhibitor and the therapeutic or diagnostic compound are used in combination but this does not necessarily mean that they are administered at the same time or via the same route.

It is possible according to the invention to use combinations of enzyme inhibitors. Such combinations of inhibitors can be directed to the same enzyme or to different enzymes, such as against the peptidases NEP and ACE or against a peptidase and an esterase.

It has been demonstrated by the inventors that administration of PA and/or other enzyme inhibitors along with peptide radioligands leads to a better stability and higher tumor uptake. This finding allows the use of radiopeptides considered thus far clinically "useless" due to extreme in vivo instability in diagnosis and therapy.

In particular embodiments of the invention the following combinations are used:
- [($^{111}$In-DOTA)Ala$^1$]SS-14 or [($^{111}$In-DOTA)Ala$^1$,$_D$Trp$^8$] SS-14 with PA and/or race
- $^{111}$In-DOTA-MG11 with PA and/or race
- $^{99m}$Tc-demotensin 6 or $^{99m}$Tc-demotensin 1 with PA and/or lisinopril
- $^{99m}$Tc-NMC analogs, such as $^{99m}$Tc-SAR-NC1 and $^{99m}$Tc-SAR-NC6 with PA
- $^{99m}$Tc-demobesin 4 or $^{111}$In-PanSarbesin 1 with PA
- $^{99m}$Tc-demobesin 1 with PA or In-JMV4168 with PA.

In another embodiment, the radiopeptide is co-administered with an enzyme substrate of reduced toxicity. This partly or totally blocks off-targeting. When the peptidase activity is inhibited by administration of a competing enzyme substrate, the competing enzyme substrate is for example a proteinaceous plasma expander such as Haemaccel or Gelofusine®.

The invention will be further illustrated in the Examples that follow and that are not intended to limit the invention in any way. In the Examples reference is made to the following figures:

FIG. 1

A: Radiochromatogram of ex vivo mouse blood 5 min after injection of [($^{111}$In-DOTA)Ala$^1$]Somatostatin-14 alone (upper panel) or with co-injection of phosphoramidon (PA 300 μg)(middle panel) or 45 min after ip injection of racecadotril (race 2.5 mg)(lower panel). The percentage of parent peptide remaining intact by PA treatment increased from 2% to 85% and by race pretreatment to >65%.

B: Biodistribution of [($^{111}$In-DOTA)Ala$^1$] Somatostatin-14 in SCID mice bearing AR4-2J tumors (rsst$_2^+$) at 4 h pi. Bars represent average uptake as % injected dose per gram (% ID/g) of at least 4 animals with standard deviation (control at 4 h, 2$^{nd}$ bars); three additional groups of animals received either excess [Tyr$^3$]octreotate (Tate, blocked—first bars) or PA (3$^{rd}$ bars), or 2.5 mg race ip 40 min prior to radioligand injection (race—4$^{th}$ bars). Bl=blood, Li=liver, He=heart, Ki=kidneys, St=stomach, In=intestines, Sp=spleen, Mu=muscle, Lu=lungs, Pa=pancreas, Fe=femur, Ad=adrenals and Tu=AR4-2J tumor. In the PA treated group, animals showed an uptake of 13.87±2.4% ID/g in the experimental tumor vs. 0.67±0.1% ID/g in the non-treated controls, while in the race group these values were 3.51±0.2% ID/g.

FIG. 2

A: Radiochromatogram of ex-vivo mouse blood 5 min after injection of [($^{111}$In-DOTA)Ala$^1$, DTrp$^8$]Somatostatin-14 alone (upper panel) or with PA (300 μg, lower panel). The percentage of parent peptide remaining intact by PA treatment is raised from 6% to 95%.

B: Biodistribution of [($^{111}$In-DOTA)Ala$^1$, DTrp$^8$]Somatostatin-14 in SCID mice bearing AR4-2J tumors (rsst$_2^+$) at 4 h pi. Bars represent average uptake as mean % injected dose per gram (% ID/g) of at least 4 animals with standard deviation (control at 4 h 2$^{nd}$ bars); two additional groups of animals received either excess Tate (100 μg, blocked—first bars) or PA (300 μg PA—3$^{rd}$ bars) or were ip pre-injected with 2.5 mg race 1 h prior to radiotracer injection (race—4$^{th}$ bars). Bl=blood, Li=liver, He=heart, Ki=kidneys, St=stomach, In=intestines, Sp=spleen, Mu=muscle, Lu=lungs, Pa=pancreas, Fe=femur and Tu=AR4-2J tumor. In the PA treated group, animals showed an uptake of 9.06±3.57% ID/g in the experimental tumor while in the race pretreated animals tumor uptake was 4.18±2.28% ID/g vs. 1.82±0.36% ID/g in the non-treated controls.

FIG. 3

A: Radiochromatogram of ex vivo mouse blood 5 min after injection of [($^{111}$In-DOTA)DGlu$^{10}$]Minigastrin(10-17) ($^{111}$In-DOTA-MG11), a truncated des-(Glu)$_5$-minigastrin analog, alone (upper panel) or with PA (300 μg PA—middle panel), or were pretreated with race (2.5 mg ip 1 h before—lower panel). The percentage of parent peptide remaining intact by PA treatment is raised from <5% to >70%.

B: Biodistribution of $^{111}$In-DOTA-MG11 in SCID mice bearing AR4-2J tumors (rCCK2R$^+$) at 4 h pi. Bars represent average uptake as mean % injected dose per gram (% ID/g) of at least 4 animals with standard deviation (control at 4 h—1$^{st}$ bars); two additional groups of animals simultaneously received PA (600 μg—2$^{nd}$ bars) or were pretreated with race (2.5 mg ip 1 h before—4$^{th}$ bars). Bl=blood, Li=liver, He=heart, Ki=kidneys, St=stomach, In=intestines, Sp=spleen, Mu=muscle, Lu=lungs, Pa=pancreas, Fe=femur and Tu=AR4-2J tumor. In the PA treated group, animals showed an uptake of 11.12±3.09% ID/g in the experimental tumor and in the race-pretreated group an uptake of 6.79±2.02% ID/g vs. 1.22±0.06% ID/g in the non-treated controls.

FIG. 4

A: Radiochromatogram of ex vivo mouse blood 5 min after injection of [$^{99m}$Tc]Demotensin 6 ([($^{99m}$Tc—N$_4$)βAla$^7$, Dab$^9$,Tle$^{12}$]NT(7-13), $^{99m}$Tc—N$_4$-βAla-Arg-Dab-Pro-Tyr-Tle-Leu-OH) alone (upper panel) or with PA (lower panel). The percentage of parent peptide remaining intact by PA treatment is raised from 52% to >90%; scaling down the dose from 300 to 30 to 3 µg did not significantly affect the protective action of PA on the peptide. However, by lowering the dose to 0.3 and 0.03 µg PA the percentage of intact peptide dropped to >60% and >55%, respectively. It is interesting to observe that co-injection of the NEP-inhibitor PA (300 µg) and the ACE-inhibitor Lisinopril (Lis—250 µg) together with the radioligand did not further increased stability versus coinjection of the radioligand with PA alone, suggesting that ACE is not involved in the catabolism of partially stabilized [$^{99m}$Tc]Demotensin 6

B: Biodistribution of [$^{99m}$Tc]Demotensin 6 in SCID mice bearing WiDr tumors (hNTS1$^+$) at 4 h pi. Bars represent average uptake as mean % injected dose per gram (% ID/g) of at least 4 animals with standard deviation (control at 4 h 2$^{nd}$ bars); three additional groups of animals received either excess NT(1-13) and PA (100 µg blocker and 300 µg PA—first bars), or PA (300 µg PA—3$^{rd}$ bars) or PA and Lis (300 µg PA+250 µg Lis—4$^{th}$ bars). Bl=blood, Li=liver, He=heart, Ki=kidneys, St=stomach, In=intestines, Sp=spleen, Mu=muscle, Lu=lungs, Pa=pancreas, Fe=femur and Tu=WiDr tumor. In the PA treated group, animals showed an uptake of 3.56±0.38% ID/g in the experimental tumor while in the PA+Lis co-injected animals tumor uptake remained at this level 3.50±0.34% ID/g vs. 1.61±0.42% ID/g in the non-treated controls. It is interesting to note that blockade was very effective in the presence of PA (0.38±0.15% ID/g).

FIG. 5

A: Radiochromatogram of ex vivo mouse blood 5 min after injection of [$^{99m}$Tc]Demotensin 1 ([($^{99m}$Tc—N$_4$)Gly$^7$] NT(7-13), $^{99m}$Tc—N$_4$-Gly-Arg-Arg-Pro-Tyr-Ile-Leu-OH) alone (upper panel) or with PA (600 µg or 300 µg PA, lower panels). The percentage of parent peptide remaining intact by PA treatment is raised from <1% to >25%; scaling down the PA dose to 30 µg resulted in only 4.5% of the original peptide surviving the first 5 min after entry into circulation. Co-injection of the radiopeptide with a cocktail of the NEP-inhibitor PA (+300 µg) and the ACE inhibitor Lis (+300 µg) raised this percentage to 56%, implying a role for ACE in the catabolism. Co-injection of Lis (+300 µg) alone increased the amount of surviving radiopeptide to only just above 16%. On the other hand pretreatment with race (2.5 mg ip 40 min prior to radioligand injection) raised the intact peptide percentage to 37%.

B: Biodistribution of [$^{99m}$Tc]Demotensin 1 in SCID mice bearing WiDr tumors (hNTS1$^+$) at 4 h pi. Bars represent average uptake as mean % injected dose per gram (% ID/g) of at least 4 animals with standard deviation (control at 4 h 2$^{nd}$ bars); three additional groups of animals received either excess NT and PA (100 µg and 300 µg PA, respectively—first bars), or PA (300 µg PA—3$^{rd}$ bars) or PA and Lis (300 µg PA+300 µg Lis—4$^{th}$ bars). Bl=blood, Li=liver, He=heart, Ki=kidneys, St=stomach, In=intestines, Sp=spleen, Mu=muscle, Lu=lungs, Pa=pancreas, Fe=femur and Tu=WiDr tumor. In the PA treated group, animals showed an uptake of 4.58±0.47% ID/g in the experimental tumor while in the PA+Lis co-injected animals tumor uptake was raised to 7.71±1.19% ID/g vs. 1.20±0.21% ID/g in the non-treated controls. It is interesting to note that blockade was very effective in the presence of PA (0.23±0.09% ID/g).

FIG. 6

A: Radiochromatogram of ex vivo mouse blood 5 min after injection of [$^{99m}$Tc]SAR-NC1 ([($^{99m}$Tc—N$_4$)Gly$^1$] NMC, [$^{99m}$Tc—N$_4$-Gly-Asn-His-Trp-Ala-Val-Gly-His-Leu-Met-NH$_2$), alone (upper panel) or with PA (300 µg-lower panel). The percentage of parent peptide remaining intact by PA treatment is raised from 30% to 68%.

B: Biodistribution of [$^{99m}$Tc]SAR-NC1 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control at 4 h—2$^{nd}$ bars); two additional groups of animals received either PA (300 µg—3$^{rd}$ bar) or excess [Tyr$^4$]BBN (100 µg—first bars) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 28.34±8.05% ID/g in the experimental tumor vs. 6.51±1.91% ID/g in the non-treated controls.

FIG. 7

A: Radiochromatogram of ex vivo mouse blood 5 min after injection of [$^{99m}$Tc]SAR-NC6 ([($^{99m}$Tc—N$_4$)Gly$^1$, Sar$^7$]NMC, [$^{99m}$Tc—N$_4$-Gly-Asn-His-Trp-Ala-Val-Sar-His-Leu-Met-NH$_2$), alone (upper panel) or with PA (300 µg-lower panel). The percentage of parent peptide remaining intact by PA treatment is raised from 35% to 70%.

B: Biodistribution of [$^{99m}$Tc]SAR-NC6 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control at 4 h—2$^{nd}$ bars); two additional groups of animals received either PA (300 µg—3$^{rd}$ bar) or excess [Tyr$^4$]BBN (100 µg—first bars) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 27.58±3.47% ID/g in the experimental tumor vs. 9.22±1.40% ID/g in the non-treated controls.

FIG. 8

A: Radiochromatogram of ex vivo mouse blood 5 min after injection of [$^{99m}$Tc]Demobesin 4 ($^{99m}$Tc—N$_4$-Pro-Gln-Arg-Tyr-Gly-Asn-Gln-Trp-Ala-Val-Gly-His-Leu-Nle-NH$_2$), alone (upper panel) or after iv co-injection of PA (30, 3 and 0.3 µg) (following panels). The percentage of parent peptide remaining intact by PA treatment is raised from 26% to >77%, >63% and 30%, respectively.

B: Biodistribution of [$^{99m}$Tc]Demobesin 4 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control at 4 h—first bars); an additional group of animals received PA (300 µg—2$^{nd}$ bar) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 35.50±7.50% ID/g in the experimental tumor vs. 11.26±1.81% ID/g in the non-treated controls.

FIG. 9

A: Radiochromatogram of ex vivo mouse blood 5 min after injection of [$^{111}$In]PanSarbesin 1 ([($^{111}$In-DOTA-PEG$_2$-DTyr-Gln-Trp-Ala-Val-βAla-His-Phe-Nle-NH$_2$) alone (upper panel) or with PA (300 µg-lower panel). The percentage of parent peptide remaining intact by PA treatment is raised from 13% to 80%.

B: Biodistribution of [$^{111}$In]PanSarbesin 1 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control at 4 h—2$^{nd}$ bars); two additional groups of animals received either PA (300 µg—3$^{rd}$ bar) or excess [Tyr$^4$]BBN (100 µg) in addition to PA (300 µg—first bars) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 20.96±2.58% ID/g in the experimental tumor vs. 3.75±0.73% ID/g in the non-treated controls. It is interesting to note that with co-injection of the blocker and PA ($1^{st}$ bar) tumor values were minimal (0.69±0.03% ID/g).

FIG. 10

A: Radiochromatogram of ex vivo mouse blood 5 min after injection of [$^{99m}$Tc]Demobesin 1 ([($^{99m}$Tc—N$_4$)(p-aminobenzyl-diglycolic acid)-[DPhe$^6$,LeuNHEt$^{13}$]BBN(6-13), alone (upper panel) or after iv co-injection of PA (300 µg—middle panel) or 45 min after ip injection of PA (600 µg—lower panel). The percentage of parent peptide remaining intact by PA treatment (either iv or ip 45 min in advance) is raised from 61% to >85%. Similar effect is achieved by injection of [$^{99m}$Tc]Demobesin 1 1 h after ip injection of race (2.5 mg) (lower panel, FIG. 10A-2) vs injection of [$^{99m}$Tc]Demobesin 1 alone (upper panel, FIG. 10A-2)

B: Biodistribution of [$^{99m}$Tc]Demobesin 1 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control at 4 h—first bars); an additional group of animals received PA (300 µg—$2^{nd}$ bars) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 18.59±0.95% ID/g in the experimental tumor vs. 12.73±0.93% ID/g in the non-treated controls.

FIG. 11

A: Radiochromatogram of ex vivo mouse blood 5 min after injection of [$^{111}$In]JMV4168 ([$^{111}$In]DOTA-βAla-βAla-JMV594, [$^{111}$In]DOTA-βAla-βAla-DPhe-Gln-Trp-Ala-Val-Gly-His-Sta-Leu-NH$_2$) alone (upper panel) or with PA (lower panel). The percentage of parent peptide remaining intact by PA treatment is raised from 64% to 98%.

B: Biodistribution of [$^{111}$In]JMV4168 in SCID mice bearing human prostate adenocarcinoma PC-3 xenografts (GRPR$^+$) at 4 h pi. Bars represent average uptake as % injected dose per gram (% ID/g) of at least 4 animals with standard deviation (control 4 h, first bars); an additional group of animals received PA (300 µg—$2^{nd}$ bars) along with the radioligand. Bl=blood, Li=liver, He=heart, Ki=kidneys, St=stomach, In=intestines, Sp=spleen, Mu=muscle, Lu=lungs, Pa=pancreas, Fe=femur and Tu=PC-3 tumor. In the PA treated group, animals showed an uptake of 23.31±11.07% ID/g in the experimental tumor vs. 10.22±2.40% ID/g in the non-treated controls.

C: A Static SPECT-CT image 1 h (upper panels) and 4 h (lower panels) after injection of [$^{111}$In]JMV4168 alone (left images) or together with PA (right images). The hGRPR$^+$ PC295 tumor on the shoulder(s) is/are excellently delineated in the PA-treated animals, whereas in the non-treated controls the uptake is significantly poorer.

FIG. 12

[111In]SP-1 control; +300 µg PA; +300 µg PA+300 µg Lis; SP-1:[(DOTA)Arg1]Substance P; SP-1: (DOTA)Arg-Pro-Lys-Pro-Gln-Gln-Phe-Phe-Gly-Leu-Met-NH2.

FIG. 13

Figure 13:
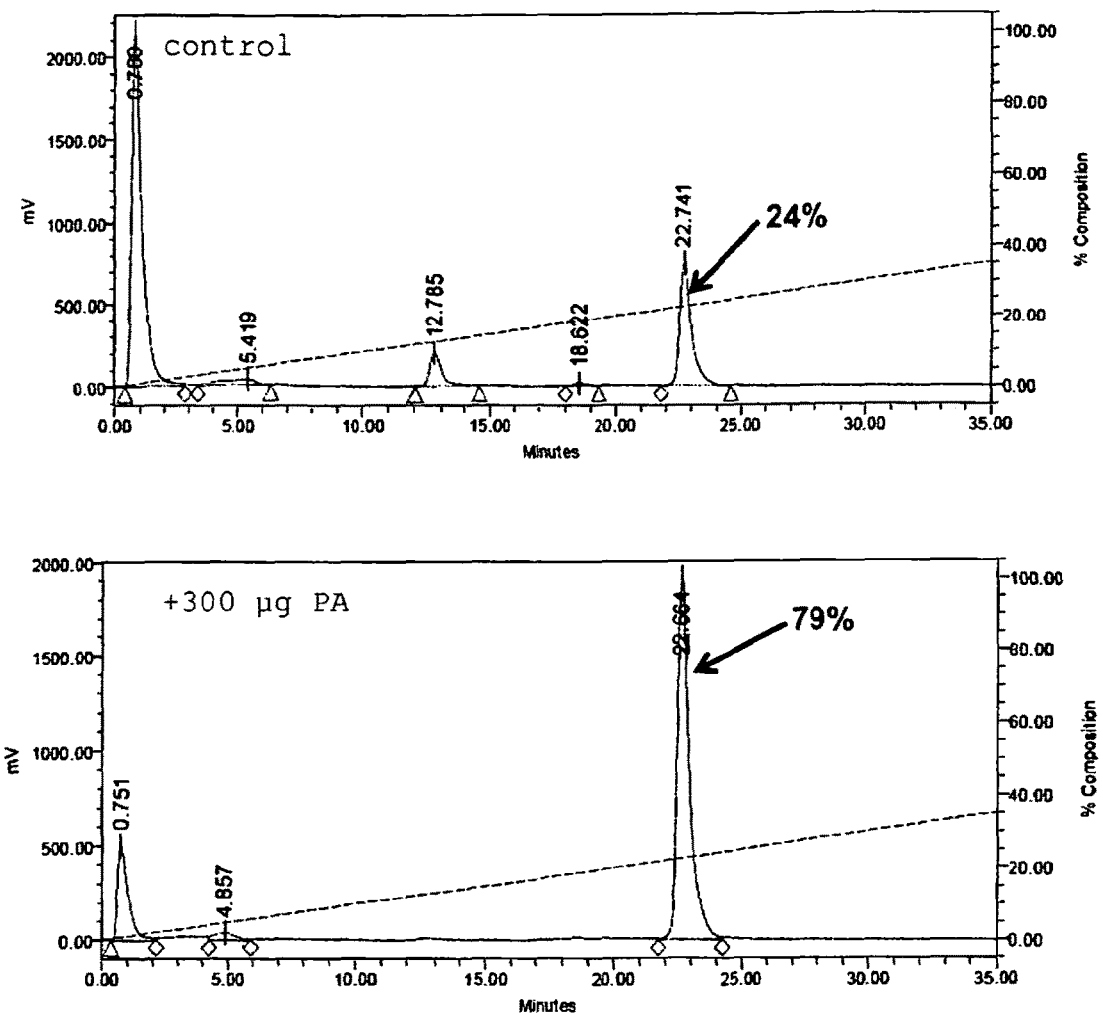

FIG. 13: [111In]SP-2 control; +300 µg PA; SP-2:[(DOTA)Arg1,Met(O2)11]Substance P; SP-2: (DOTA)Arg-Pro-Lys-Pro-Gln-Gln-Phe-Phe-Gly-Leu-Met(O2)-NH2.

FIG. 14

Figure 14:
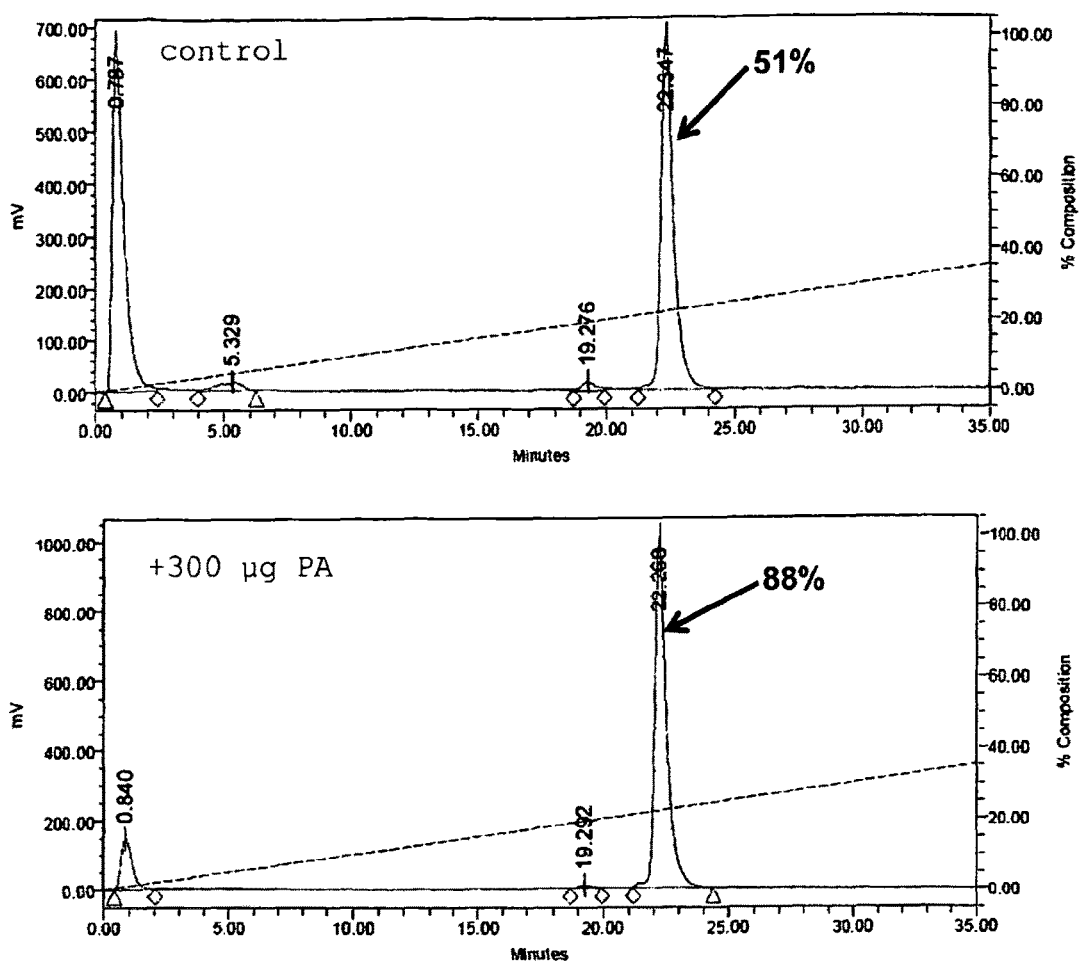

FIG. 14: [111In]SP-3 control; +300 µg PA; SP-3:[(DOTA)Arg1,Sar9,Met(O2)11]Substance P; SP-3: (DOTA)Arg-Pro-Lys-Pro-Gln-Gln-Phe-Phe-Sar-Leu-Met(O2)-NH2.

FIG. 15

Figure 15:
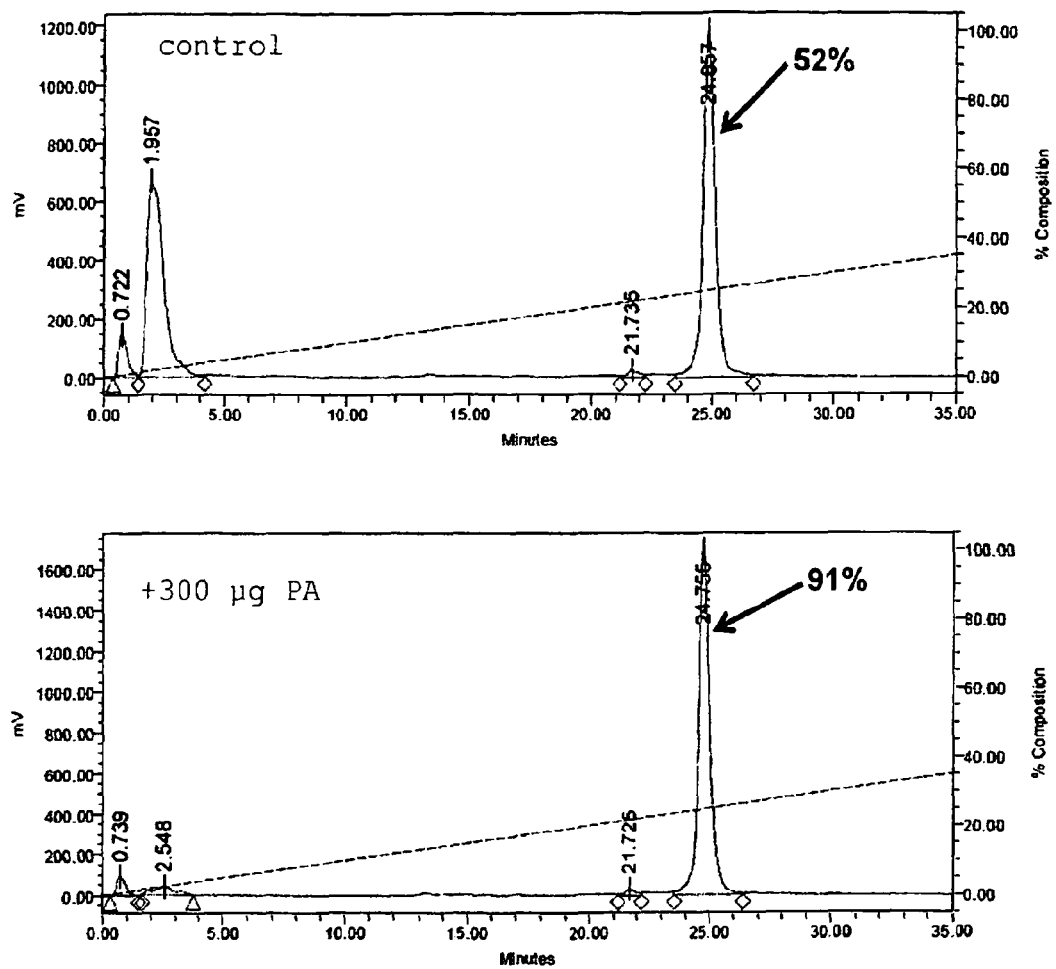

FIG. 15: [111In]MSH-1 control; +300 µg PA; MSH-1: [(DOTA)Ser1,Nle4]☐-MSH; MSH-1: (DOTA)Ser-Tyr-Ser-Nle-Glu-His-Phe-Arg-Trp-Gly-Lys-Pro-Val-NH2.

FIG. 16

Figure 16:
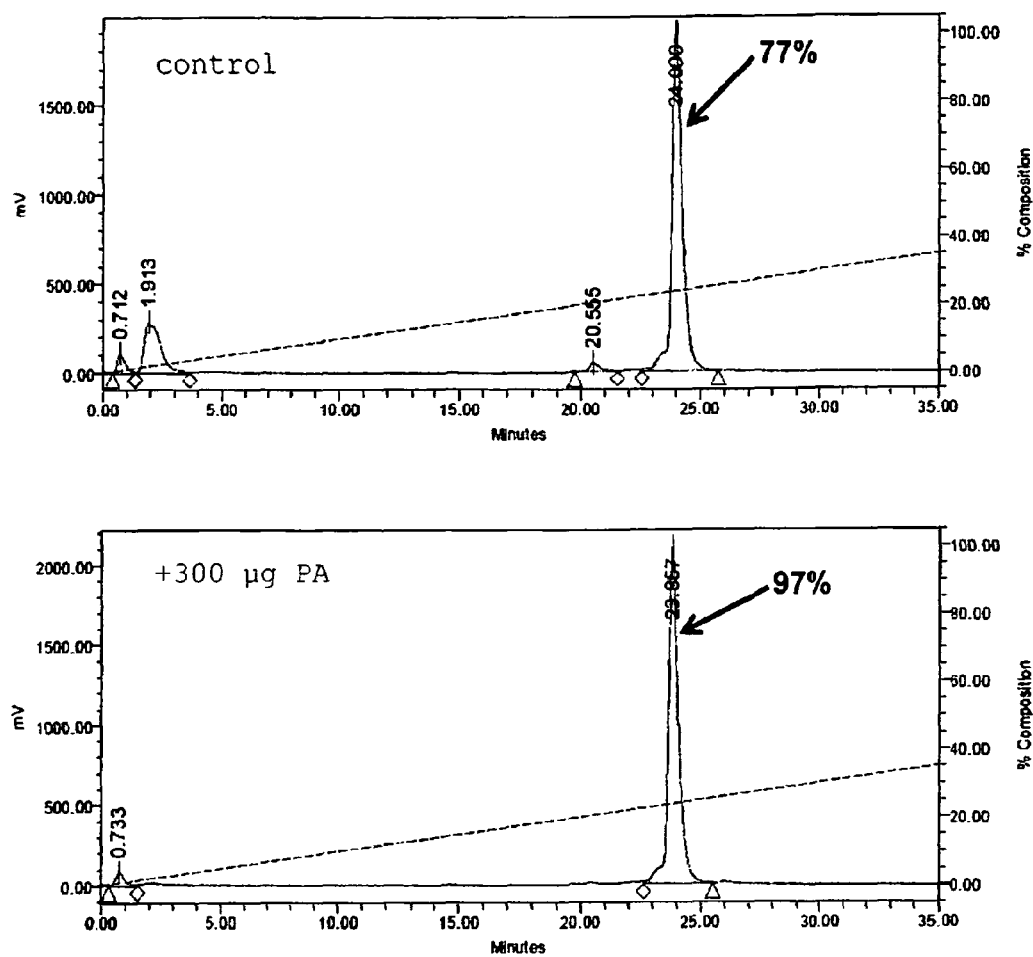

FIG. 16: [111In]MSH-2 control; +300 µg PA; MSH-2: [(DOTA)Ser1,Nle4,DPhe7]☐-MSH; MSH-2: (DOTA)Ser-Tyr-Ser-Nle-Glu-His-DPhe-Arg-Trp-Gly-Lys-Pro-Val-NH2.

FIG. 17

Figure 17:
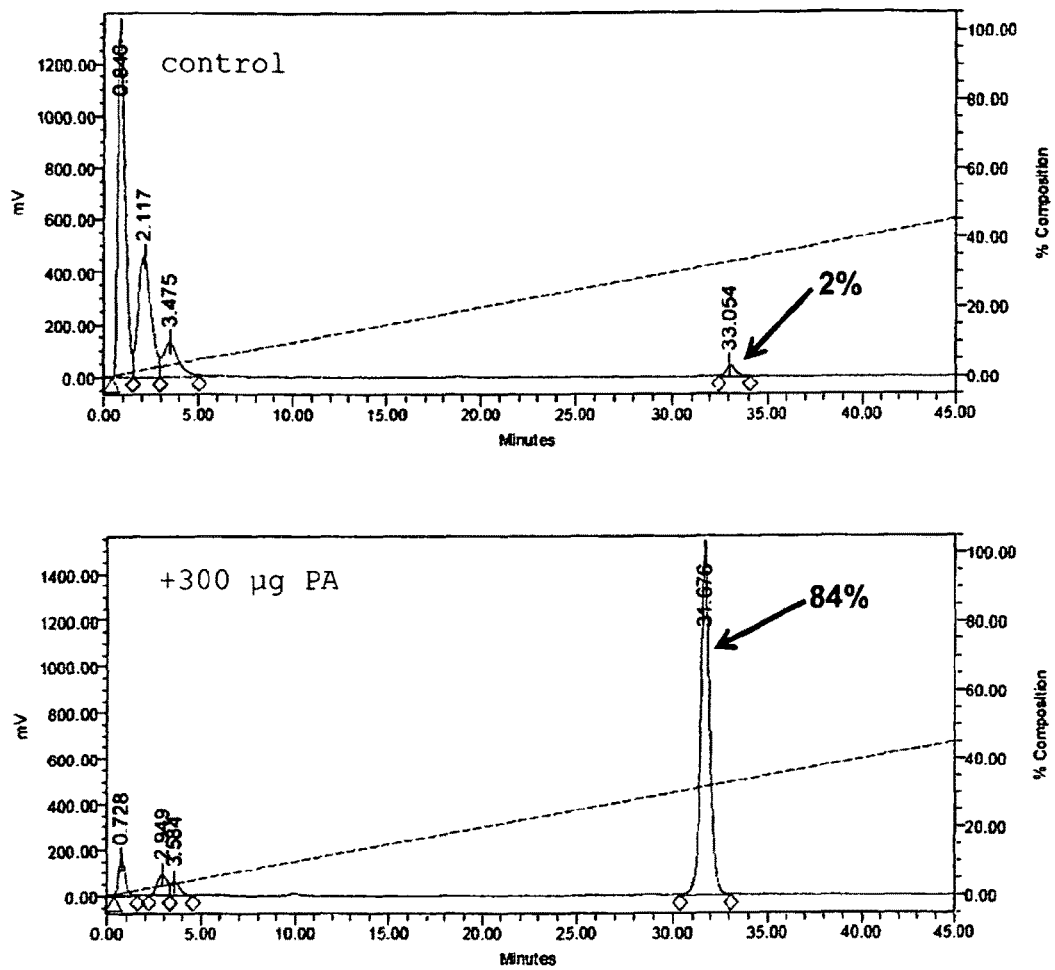

FIG. 17: [111In]CTP-1 control; +300 µg PA; CTP-1:: For-Nle-Leu-Phe-Nle-Tyr-Lys(DOTA)-OH (Chemotactic peptide-1).

EXAMPLE 1

Somatostatin-14

Native somatostatin-14 elicits its physiological effects after binding to somatostatin receptors comprising five subtypes, $sst_{1-5}$. Due to the high density expression of $sst_2$ in neuroendocrine tumors synthetic stable $sst_2$-preferring radioligands have been developed, while the in vivo application of SS14 was abandoned due to its rapid in vivo degradation. Interest for the development of a pansomatostatin-like analog (one binding to all five $sst_{1-5}$ with a high affinity) was revived by the fact that $sst_{1-5}$ are expressed alone or in various combinations in more types of human tumors. The inventors have recently developed SS14 analogs derivatized at the N-terminus with DOTA to allow for trivalent radiometal binding, such as $^{111}$In.

In Vivo Stability

To study in vivo stability and the effect of vasopeptidase inhibition in prolonging biological half life of $^{111}$In[(DOTA)Ala$^1$]SS14 and $^{111}$In[(DOTA)Ala$^1$,DTrp$^8$]SS14, each radiopeptide was injected in the tail vein of Swiss albino mice alone or with the NEP inhibitor phosphoramidon (PA, 300 µg). Whole blood was collected 5 min postinjection (pi), blood cells were removed and major proteins were precipitated and then the supernatant was analyzed by RP-HPLC coupled to a gamma detector.

Alternatively, the dual NEP and ACE inhibitor racecadotril (race; 2.5 mg) was ip injected 45-60 min prior to radioligand injection and the same procedure was followed as described above.

Figure 2A:
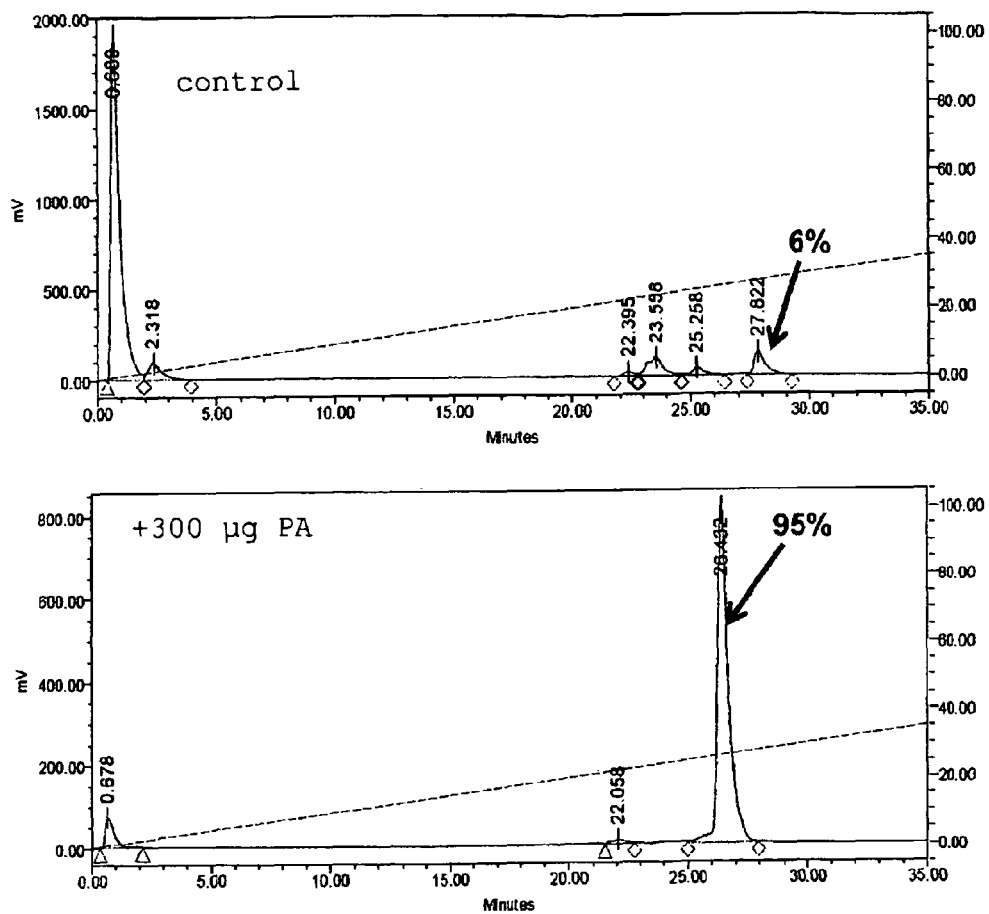

Representative radiochromatograms are shown in FIG. 1A and FIG. 2A. Indeed, both radiolabeled analogs showed very poor stability in vivo despite the common N-terminus modification and the Trp$^8$ substitution by DTrp$^8$ in the second analog, with the percentages of intact peptides not exceeding 2% and 6%, respectively. By PA co-injection these percentages spectacularly rose above 85% and 95%, respectively. Pretreatment with race provoked similar but less pronounced stabilization effects, with the respective percentage rising to >65%.

Tumor Uptake

Figure 1B:
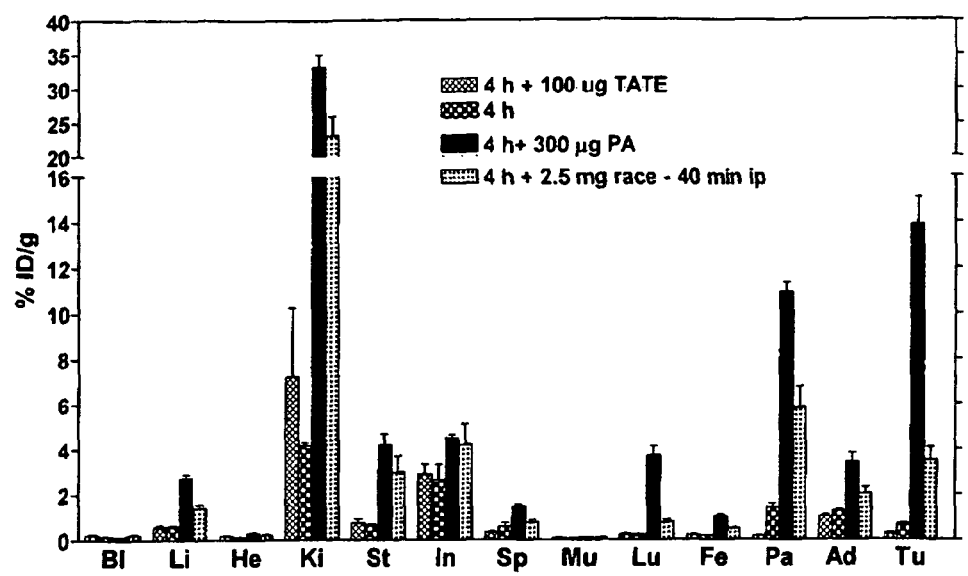
Figure 2B:
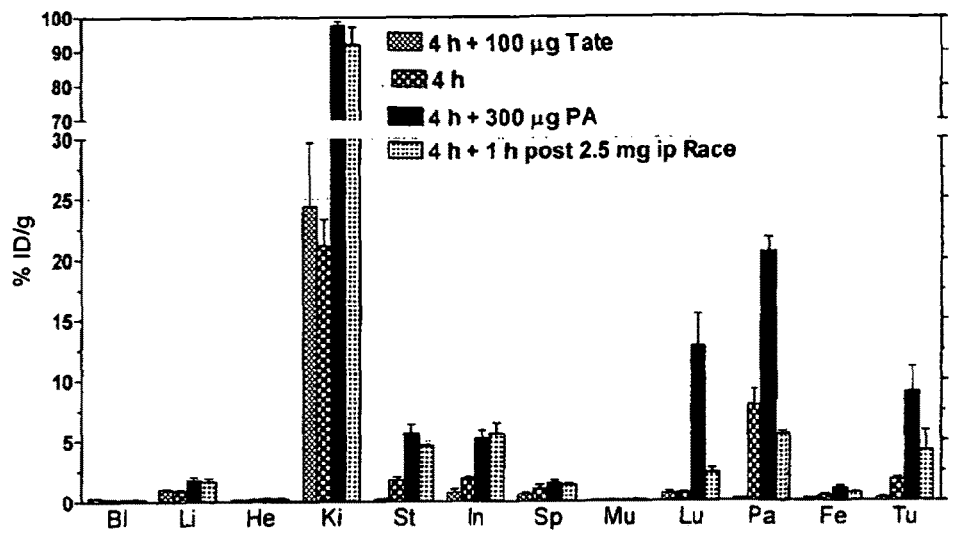

Of great importance is the direct translation of PA-(or race) induced radiopeptide stabilization into meaningful and dramatic increase of tumor uptake in animals. Indeed, uptake in the $rsst_2^+$ AR4-2J tumor after injection of $^{111}$In [(DOTA)Ala$^1$]SS14 reached 13.87±2.4% ID/g in the PA-treated group at 4 h pi vs. 0.67±0.1% ID/g in the non-treated controls, while in the race pre-treated mice tumor values reached 3.51±0.2% ID/g, as presented in FIG. 1B. The corresponding values for the DTrp$^8$-analog, shown in FIG. 2B, reach 9.06±3.57% ID/g (PA group), 4.18±2.28% ID/g (race group) and 1.82±0.36% ID/g (non-treated controls).

The above unexpected findings are of great significance for the applicability of radiolabeled SS14 analogs as pan-somatostatin-like diagnostic and therapeutic tools. More so, in view of the fact that the pharmacological character of the native hormone is preserved. Recent efforts to develop synthetic pansomatostatin-like analogs led to radioligands that bind differently to some or all sst-subtypes, or do not efficiently internalize or show disappointingly poor pharmacokinetics. Accordingly, the combination of SS14 based radioligands with PA provides new molecular tools of potentially higher diagnostic sensitivity and therapeutic efficacy, given the inherent capacity of SS14 per se to most efficiently interact with all five $sst_{1-5}$.

EXAMPLE 2

Gastrin

The overexpression of cholecystokinin-2 receptors (CCK2R) in many human tumors, such as in medullary thyroid cancer (MTC), small cell lung cancer, ovarian cancer and others, renders them attractive molecular targets for CCK2R-targeted diagnosis and therapy with radiolabeled CCK- and gastrin-derived probes. Most of the gastrin based radioligands show high CCK2R-affinity and metabolic stability but display undesirable kidney accumulation. On the other hand, the non-kidney accumulating radiolabeled CCKs or des(Glu)$_5$-truncated gastrins suffer from very rapid in vivo degradation and/or lower CCK2R affinity. As a result, the search for clinically useful radiolabeled CCKs and gastrins for CCK2R-targeted diagnosis and therapy is currently intense. ($^{111}$In-DOTA)DGlu$^{10}$]Minigastrin(10-17) ($^{111}$In-DOTA-MG11) was identified as one of the most rapidly degraded des(Glu)$_5$-minigastrin radioligands, unable to achieve satisfactory CCK2R-targeting in mouse models.

In Vivo Stability

Figure 3A:
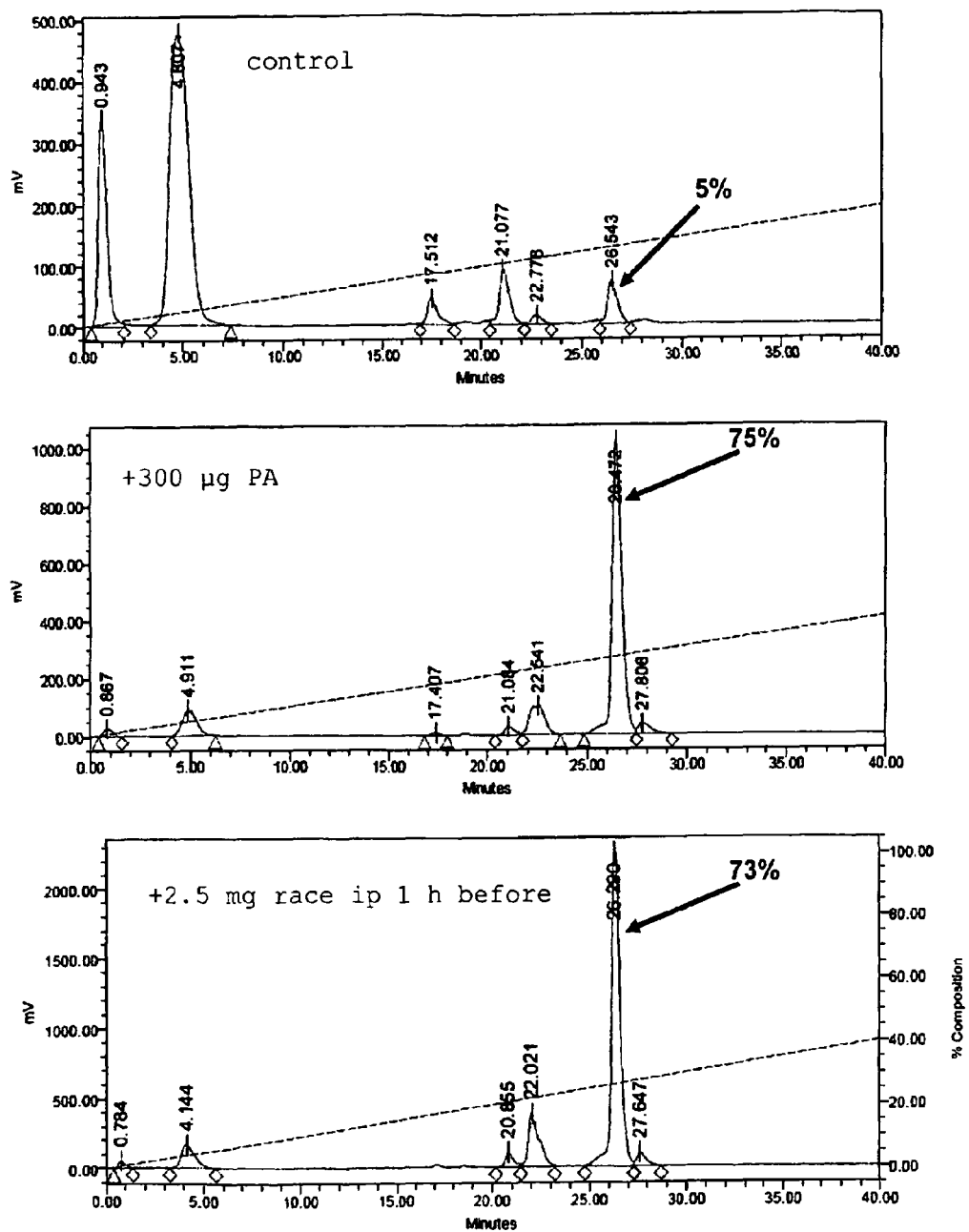

To test the in vivo stability, $^{111}$In-DOTA-MG11 was injected in the tail vein of Swiss albino mice and 5 min afterwards blood was collected, blood cells were removed and major proteins were precipitated and then the supernatant was analyzed by RP-HPLC coupled to a gamma detector. As shown in the radiochromatogram of FIG. 3A, the major part of $^{111}$In-DOTA-MG11 was consumed during this period (<5% intact peptide still detected), in agreement with previous reports. Further, $^{111}$In-DOTA-MG11 was co-injected together with PA or injected 1 h after ip injection of race (2.5 mg) in more mice and the same protocol was followed as above. Amazingly, the percentage of $^{111}$In-DOTA-MG11 found intact in the blood of the PA-treated mice was raised from <5% to 75% and in the race-pretreated mice to 73%.

Tumor Targeting

Figure 3B:
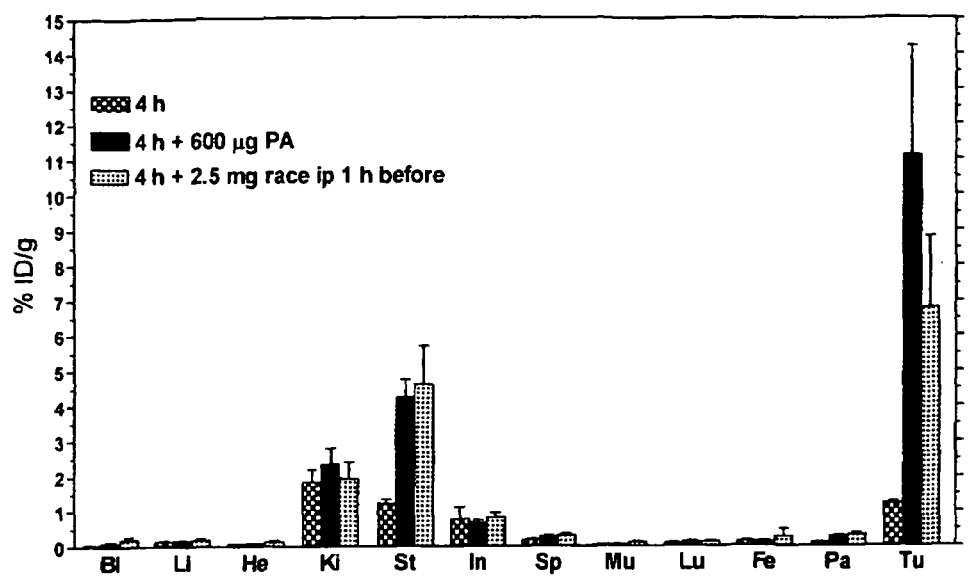

The unpredictable "in vivo protection" of $^{111}$In-DOTA-MG11 conveyed by PA or race, albeit not full, translated into a surprisingly huge increase of CCK2R-targeting in an experimental tumor in mice. Biodistribution results in SCID mice bearing rCCK2R$^+$ AR4-2J tumors 4 h after injection of $^{111}$In-DOTA-MG11 alone or together with PA or 1 h after ip injection of race are shown in FIG. 3B. Most astonishingly, tumor values reached 11.11±3.09% ID/g in the PA-receiving group vs. 1.22±0.06% ID/g in the untreated controls, whereas in the race-treated group this value reached 6.79±2.02% ID/g.

Kidney Uptake

Of particular relevance is the fact that PA administration, while causing an astounding >9 fold increase in the tumor, exerted absolutely no effect on kidney uptake. The same observation was made for the race group as well. As a result, unprecedented tumor-to-kidney ratios were achieved after injection of $^{111}$In-DOTA-MG11 by PA or race treatment.

This finding fulfils an important prerequisite for effective radionuclide therapy of CCK2R$^+$-tumors. This perspective is especially relevant for MTC patients, who are lacking therapeutic options at an advanced and disseminated state of the disease.

EXAMPLE 3

Neurotensin (NT)

The expression of neurotensin subtype 1 receptor (NTS1R) in human cancers, such as Ewing's sarcomas, ductal exocrine pancreatic carcinomas, colorectal cancer and meningiomas has been well documented. Especially for exocrine pancreatic cancer there is an urgent need for new effective clinical tools for its early diagnosis and therapy due to its high prevalence and very poor prognosis. Accordingly, several new neurotensin (NT) analogs have been developed and radiolabeled with $^{99m}$Tc or with trivalent metals (Maes V et al, 2006; Maina T et al, 2007; De Visser M et al 2003) with a few already evaluated in the clinic. However, results have been disappointing so far and one of the main reasons suspected for sub-optimal targeting is poor radioligand in vivo stability.

As stability has been so far exclusively investigated in blood plasma in vitro and "stabilized" radiolabeled NTs performed poorly in patients, the inventors decided to test stability in vivo using one such analog, [$^{99m}$Tc]Demotensin 6 ($^{99m}$Tc—N$_4$-βAla-Arg-Dab-Pro-Tyr-Tle-Leu-OH). This analog, while stable in plasma of mouse and patients in vitro failed to delineate NTS1R$^+$ cancers in vivo in man despite its good affinity and internalization capacity.

Figures 1, 4A:
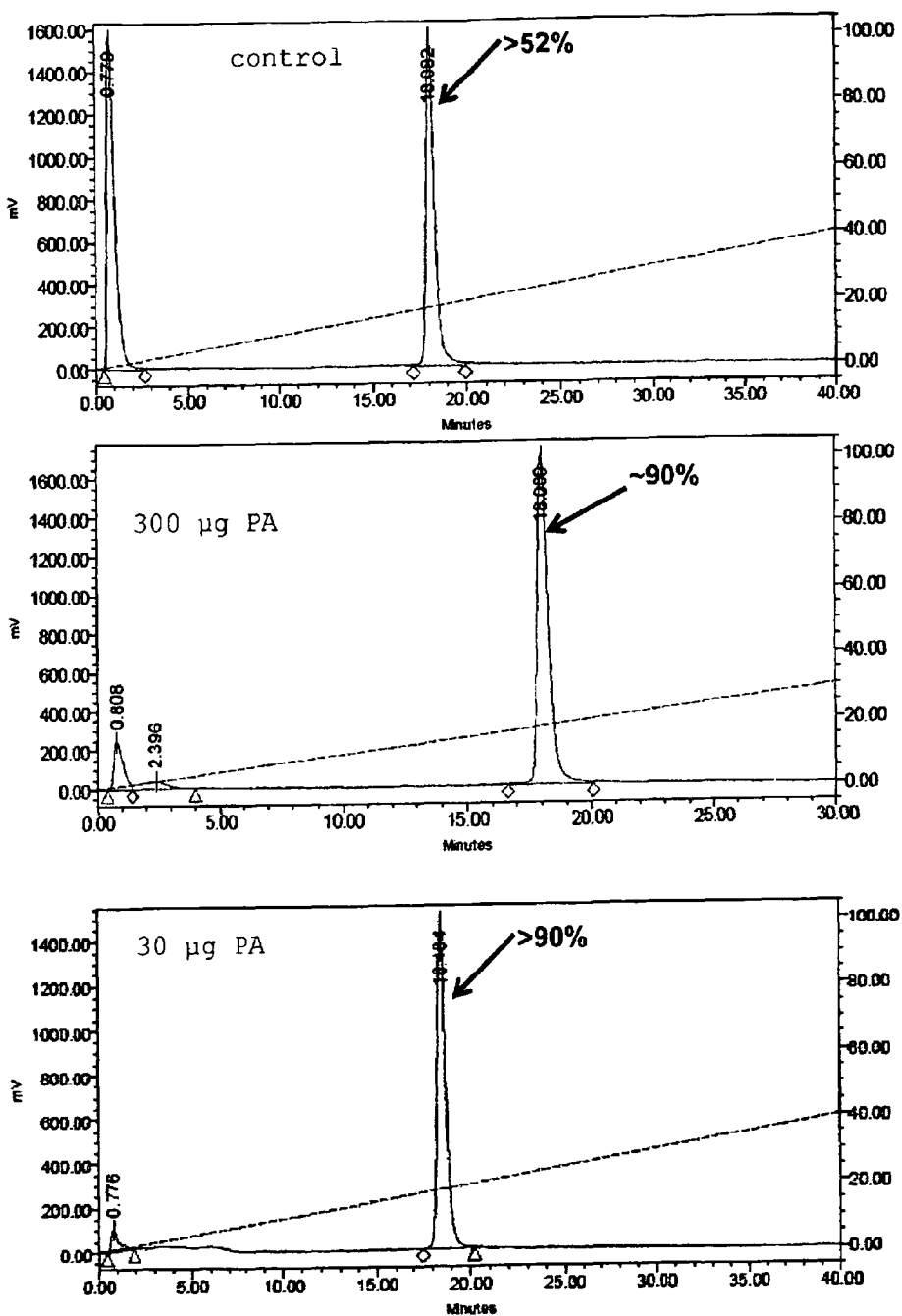

For ex vivo blood analysis, [$^{99m}$Tc]Demotensin 6 was injected in the tail vein of Swiss albino mice and blood collected 5 min thereafter was analyzed as previously described. The effect of PA on stability was studied by co-injection of PA along with [$^{99m}$Tc]Demotensin 6. Furthermore, a PA dose study was performed with the PA injected dose ranging from 300 µg down to 0.03 µg and results are summarized in FIG. 4A.

Unexpectedly and while [$^{99m}$Tc]Demotensin 6 was found >90% stable during in vitro incubation with mouse and human plasma (Maina T et al, 2007; Gabriel M et al, 2011), in vivo it is degraded by half (52%) within 5 min already. Most significantly, the inventors were able to observe a direct effect of PA on the in vivo stability of the radioligand, which varied with the administered PA-dose implying a major role of NEP in its catabolism.

Thus, the percentage of [$^{99m}$Tc]Demotensin 6 remaining intact by PA 300 µg co-injection rose to >90% and remained at this high level even by scaling down the PA dose to 30 µg initially and then to 3 µg. However, by further reducing the dose to 0.3 µg and finally 0.03 µg PA the percentage of intact peptide dropped to >60% and >55%, respectively. It is interesting to observe that co-administration of the ACE inhibitor Lis (300 µg) and PA (300 µg) showed identical results as when PA (300 µg) was injected alone.

Figures 2, 4A:
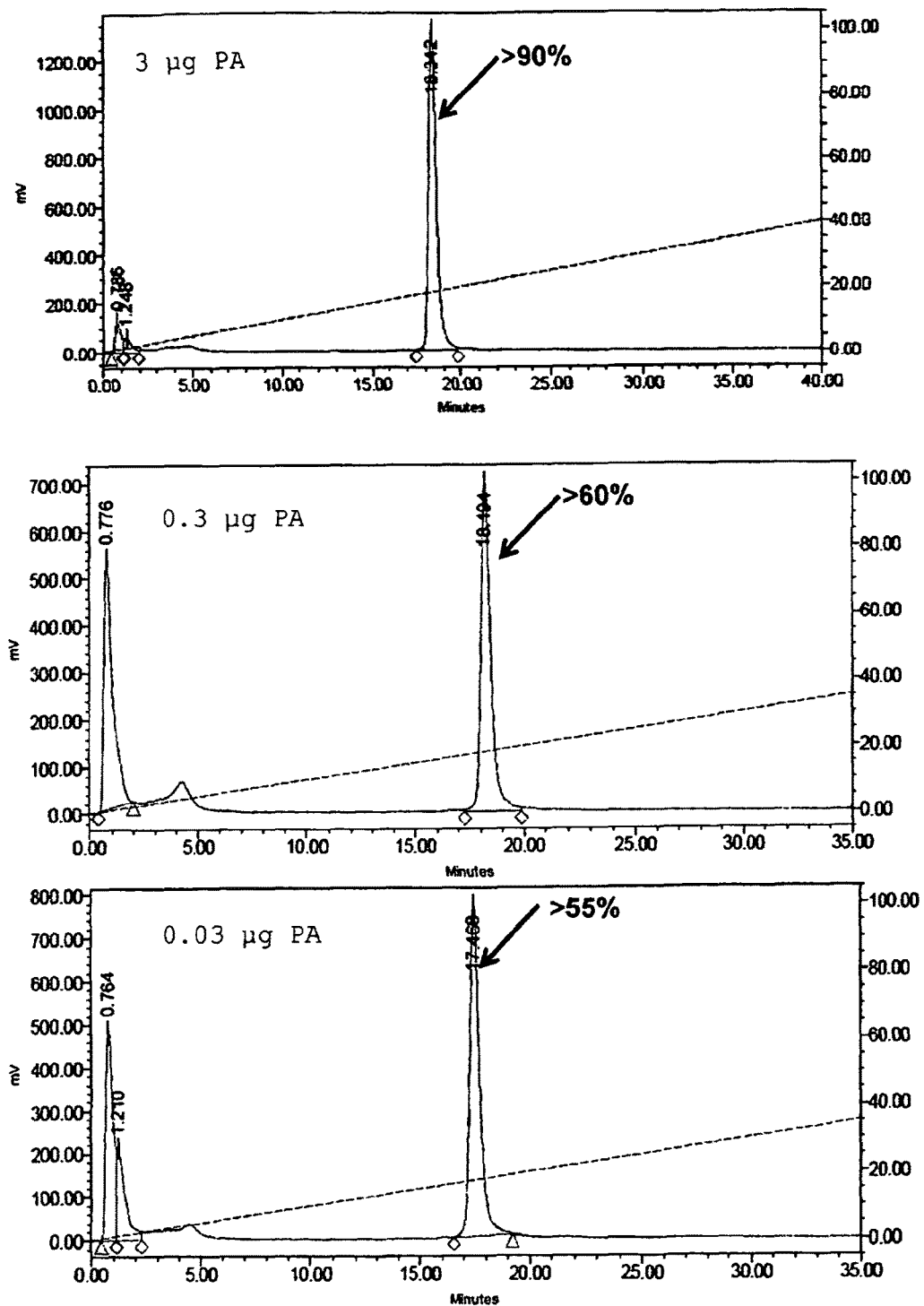
Figures 3, 4A:
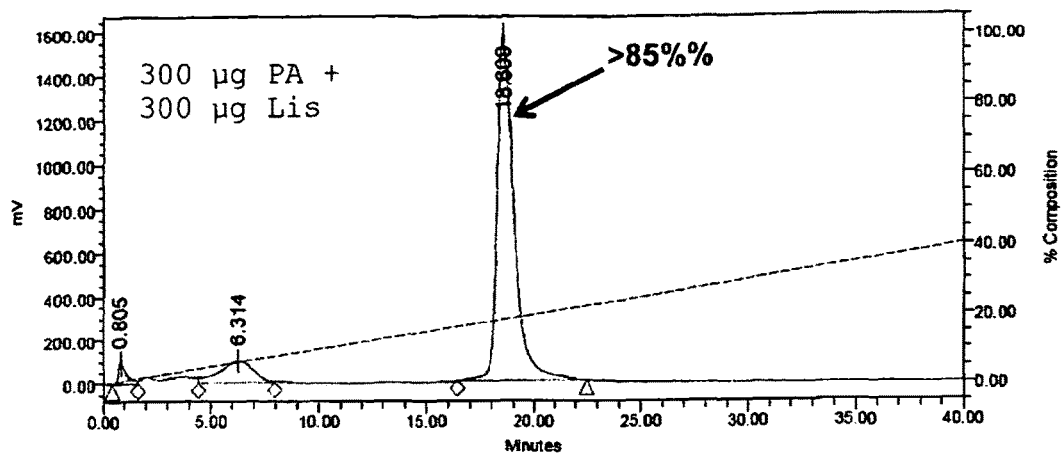
Figure 4B:
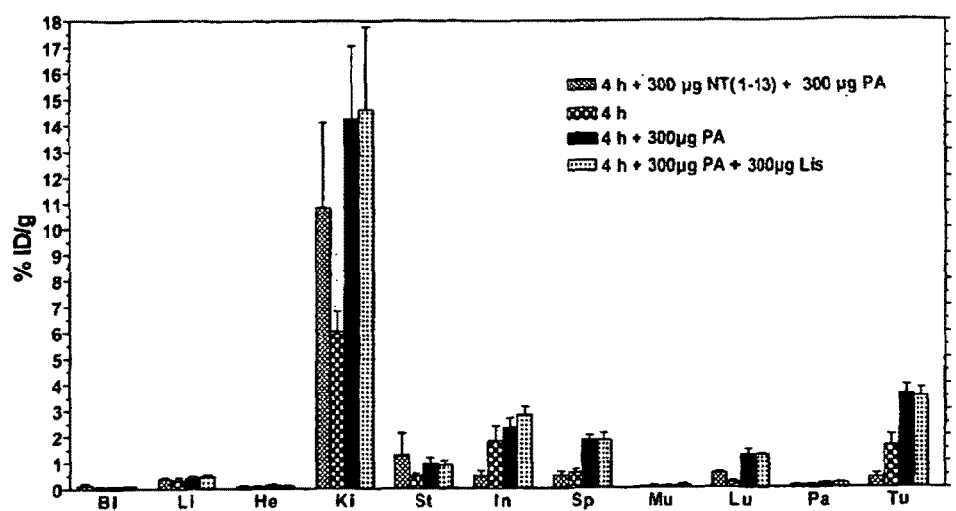

In FIG. 4B the effects of such regimens on SCID mice bearing the human colon adenocarcinoma WiDr tumor (a hNTS1R$^+$ tumor) on enhancing in vivo tumor targeting are presented. Thus, in the group receiving 300 µg PA along with the radioligand, animals showed an uptake of 3.56±0.38% ID/g in the experimental tumor, while in the PA+Lis co-injected animals tumor uptake remained at this level 3.50±0.34% ID/g vs. 1.61±0.42% ID/g in the non-treated controls, suggesting that NEP is only implicated in the catabolism of [$^{99m}$Tc]Demotensin 6 and the radiopeptide is stable against ACE. It is also interesting to note that blockade was very effective in the presence of PA (0.38±0.15% ID/g), showing that the PA-induced increase on the tumor is specific and NTS1R-mediated.

Figures 1, 5A:
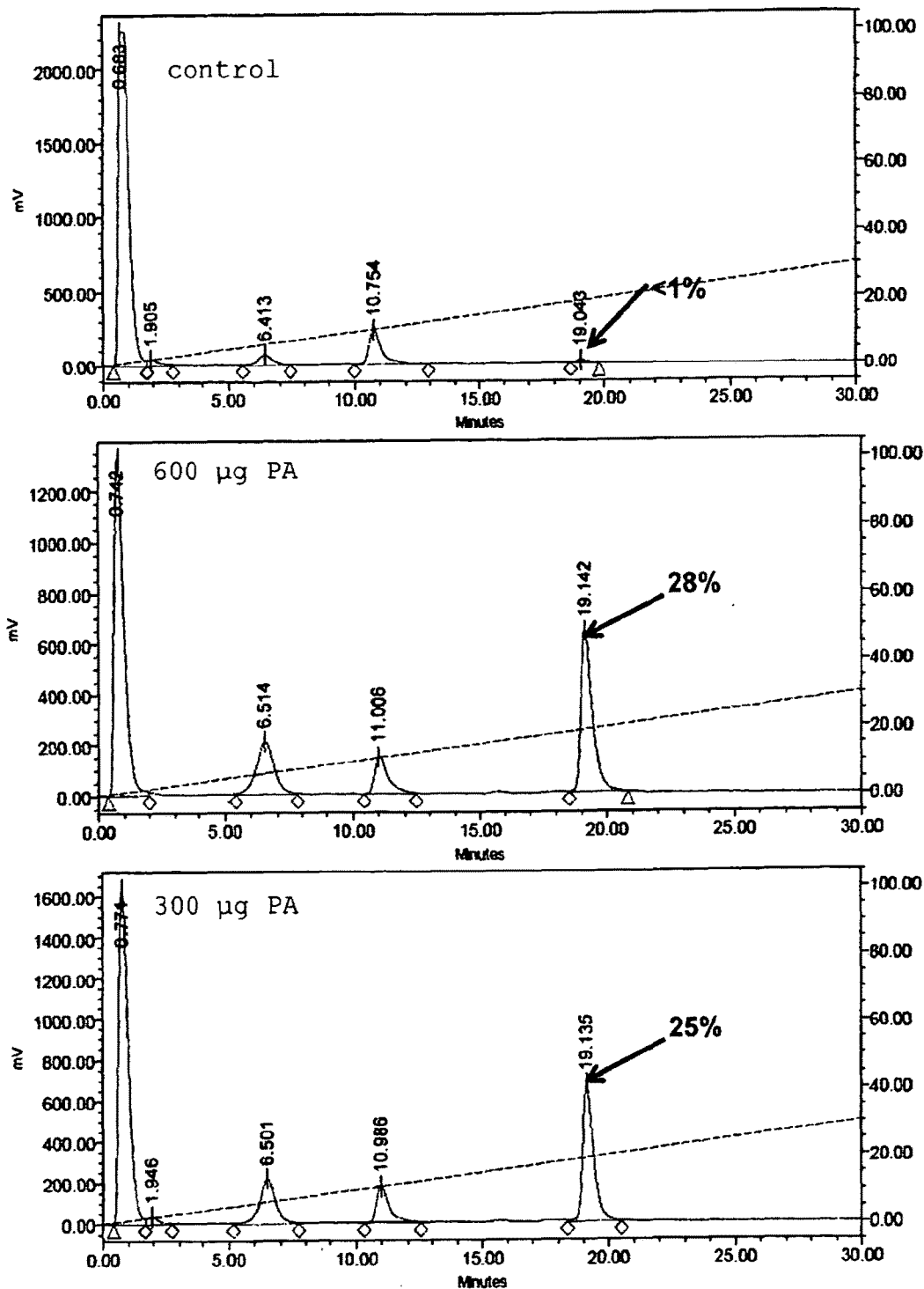
Figure 5A:
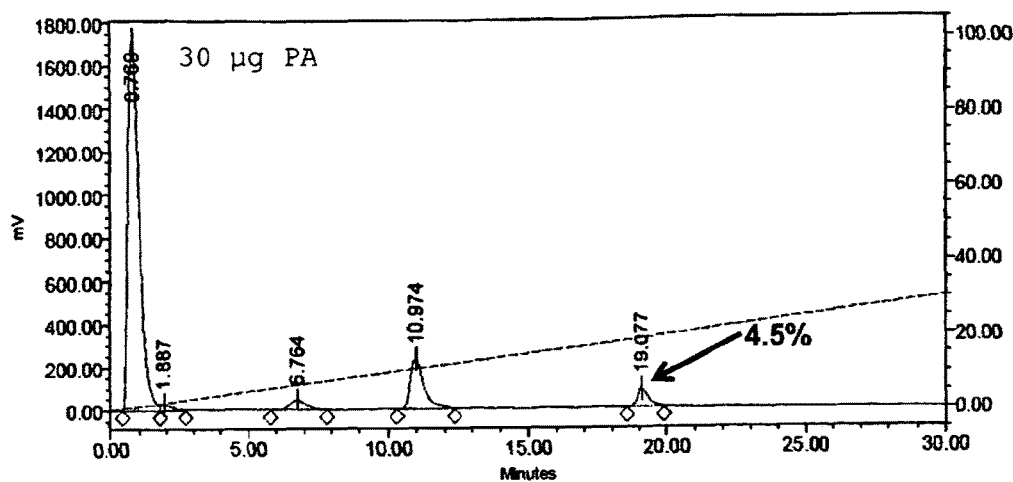
Figure 2:
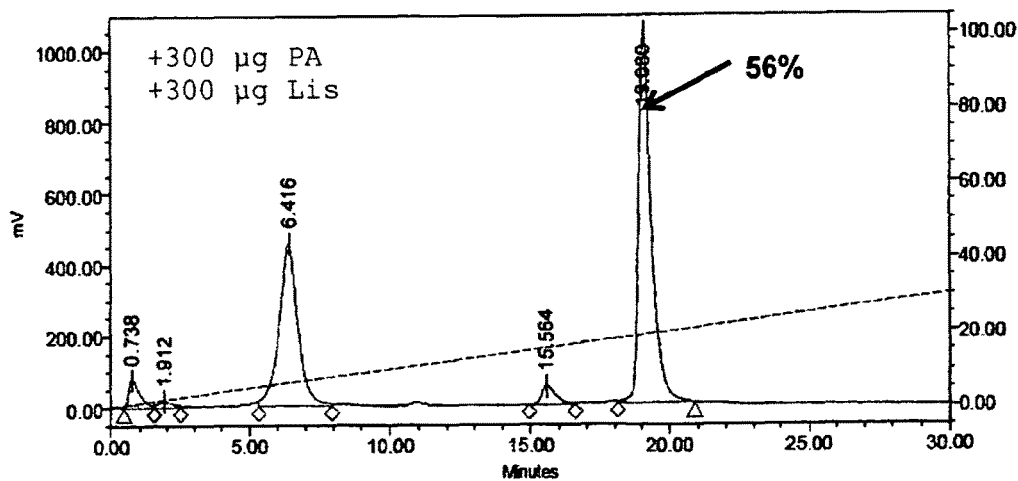
Figures 3, 5A:
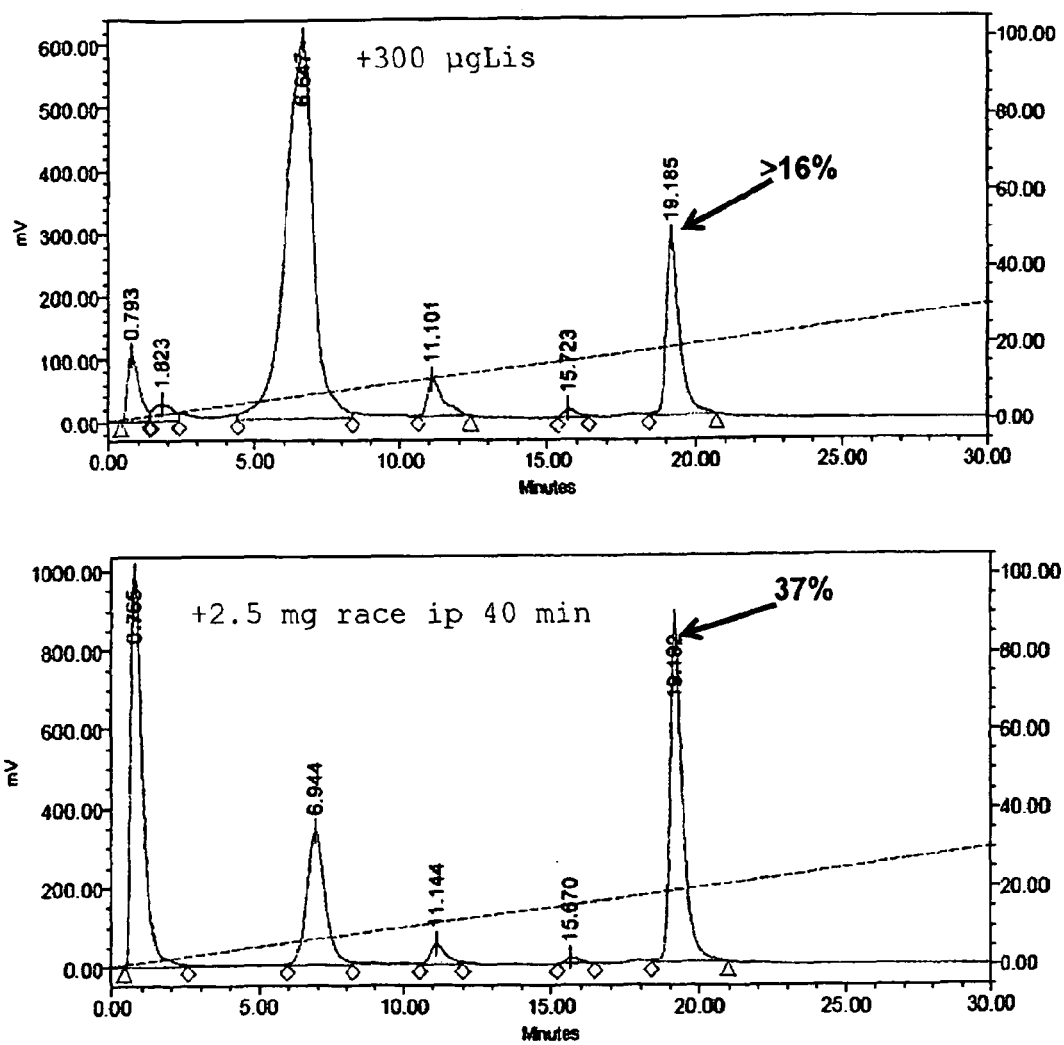

Similarly to the doubly stabilized [$^{99m}$Tc]Demotensin 6 radiotracer, the inventors were further interested to investigate the effects of PA on [$^{99m}$Tc]Demotensin 1 ([($^{99m}$Tc—N$_4$)Gly$^7$]NT(7-13), $^{99m}$Tc—N$_4$-Gly-Arg-Arg-Pro-Tyr-Ile-Leu-OH) wherein the original NT(8-13) peptide fragment is preserved. As shown in FIG. 5A less than 1% intact peptide survived 5 min in vivo as opposed to the 52% found after administration of [$^{99m}$Tc]Demotensin 6 demonstrating the clearly positive impact of strategic Arg$^9$ and Ile$^{12}$ replacement by Dab and Tle, respectively, on the in vivo stability of [$^{99m}$Tc]Demotensin 6. Co-injection of 600 µg or 300 µg PA increased the percentage of [$^{99m}$Tc]Demotensin 1 detected in mouse blood to 28% and 25%, respectively.

In contrast to [$^{99m}$Tc]Demotensin 6, co-injection of [$^{99m}$Tc]Demotensin 1 and 30 µg PA failed to sufficiently stabilize the radiopeptide, with only 4.5% still found in mouse blood. This finding suggests that other enzymes in addition to NEP are involved in the in vivo catabolism of [$^{99m}$Tc]Demotensin 1.

In order to elucidate such involvement, the inventors have co-injected 300 µg PA and 300 µg of the ACE inhibitor Lis along with the radioligand. This inhibitor combination resulted in an overall 56% of intact peptide surviving in mice during 5 min whereas co-injection of 300 µg PA alone led to only 25% intact peptide under the same experimental protocol. It is interesting to note that Lis alone was able to "protect" [$^{99m}$Tc]Demotensin 1 only up to 16%. Furthermore, the pattern of metabolites found by PA treatment significantly differs from the metabolic pattern after Lis treatment (FIG. 5A) indicating that the two enzymes attack different bonds of the peptide chain. When ip pre-injecting race (2.5 mg) to the animals prior to [$^{99m}$Tc]Demotensin 1 injection an overall of 37% peptide remains intact in the circulation.

Figure 5B:
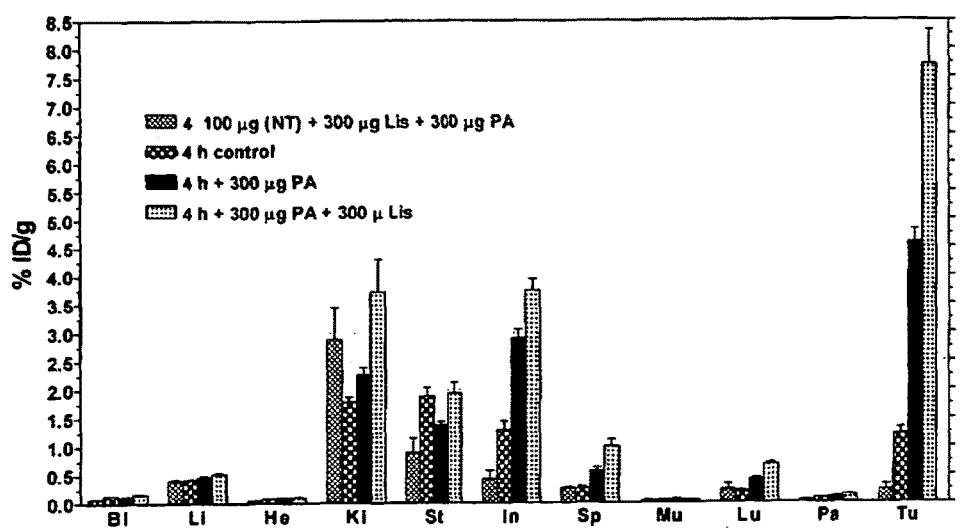

In FIG. 5B the effects of above regimens on SCID mice bearing WiDr tumors (hNTS1R$^+$) on enhancing in vivo tumor targeting are shown. Thus, in the group receiving 300 µg PA along with the radioligand, animals showed a tumor uptake of 4.58±0.47% ID/g, while in the PA+Lis co-injected animals tumor uptake was raised to 7.71±1.19% ID/g vs. 1.20±0.21% ID/g in the non-treated controls, suggesting that both NEP and ACE are implicated in the catabolism of the radiopeptide contrasting [$^{99m}$Tc]Demotensin 6 which is stable against ACE. It is also interesting to note that blockade was very effective in the presence of PA and Lis (0.23±0.09% ID/g), showing that the PA+Lis-induced increase on the tumor is specific and NTS1R-mediated.

EXAMPLE 4

Neuromedin C (NMC)

The high density expression of gastrin releasing peptide receptors (GRPRs) in many frequently occurring human cancers, such as prostate and breast cancer, gastrinomas, small cell lung cancers and others, provides the opportunity for their diagnosis and therapy using radiolabeled bombesin-like analogs. Neuromedin C (NMC) is the C-terminal decapeptide fragment (H-Gly-Asn-His-Trp-Ala-Val-Gly-His-Leu-Met-NH$_2$), of native human GRP binding with a high affinity with GRPR. The inventors have recently developed a series of NMC analogs functionalized at the N-terminus with acyclic tetraamines for stable binding of $^{99m}$Tc, SAR-NCs, as candidates for the diagnostic imaging of GRPR-expressing tumors.

Figures 1, 6A:
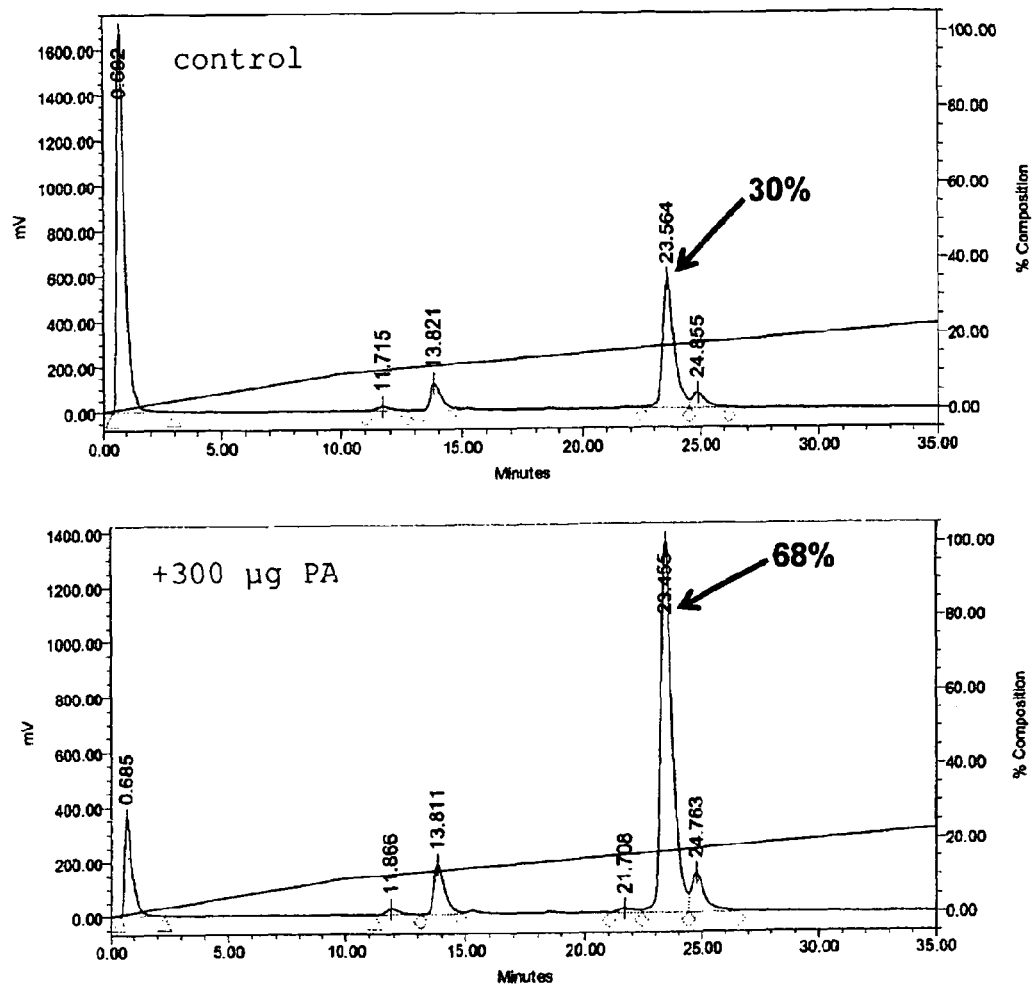
Figure 7A:
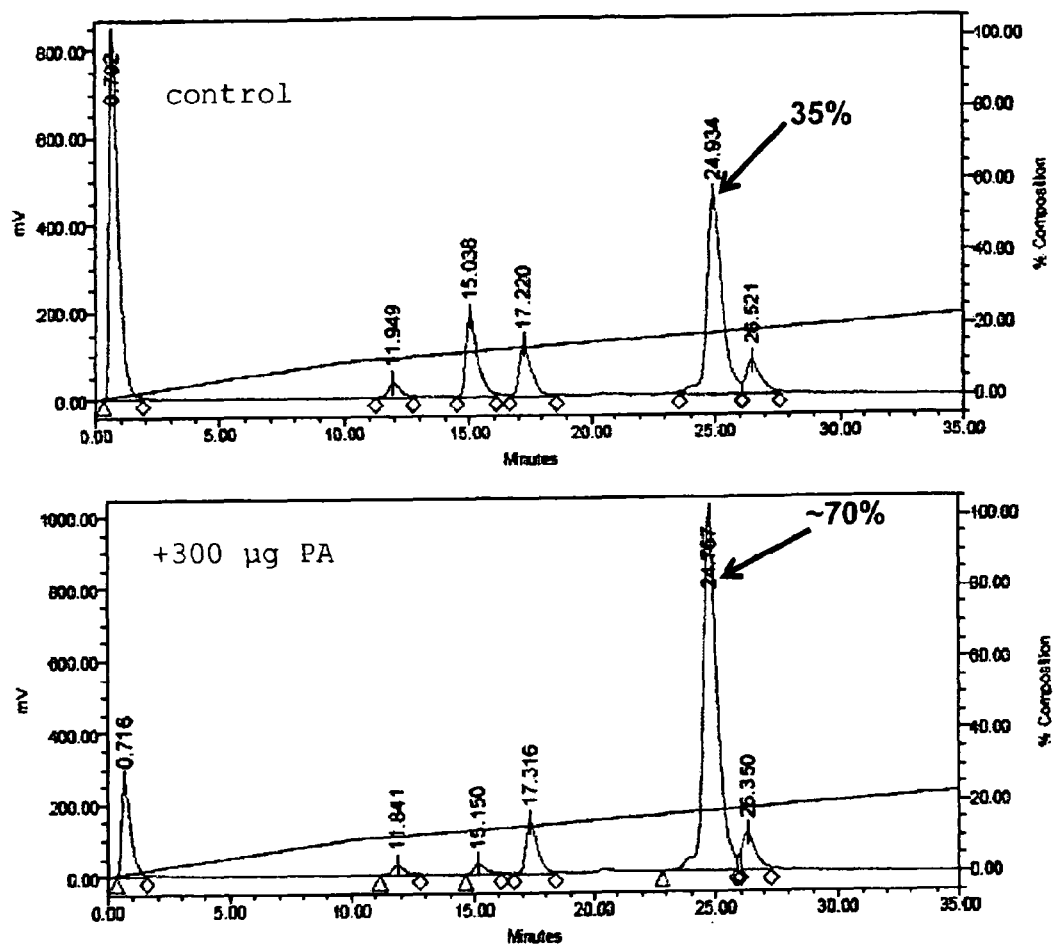

The in vivo stability of [$^{99m}$Tc]SAR-NC1 ([($^{99m}$Tc—N$_4$)Gly$^1$]NMC) and of [$^{99m}$Tc]SAR-NC6 ([($^{99m}$Tc—N$_4$)Gly$^1$, Sar$^7$]NMC) was tested as described above by collecting blood 5 min after injection of radioligand alone or together with 300 µg PA in Swiss albino mice. As shown in FIG. 6A and FIG. 7A, respectively, the amount of in vivo surviving parent peptide was 30% and 35%. PA (300 µg) treatment doubled this percentage (>68% and 70%, respectively) implicating NEP again in the catabolism of these analogs.

Figure 6B:
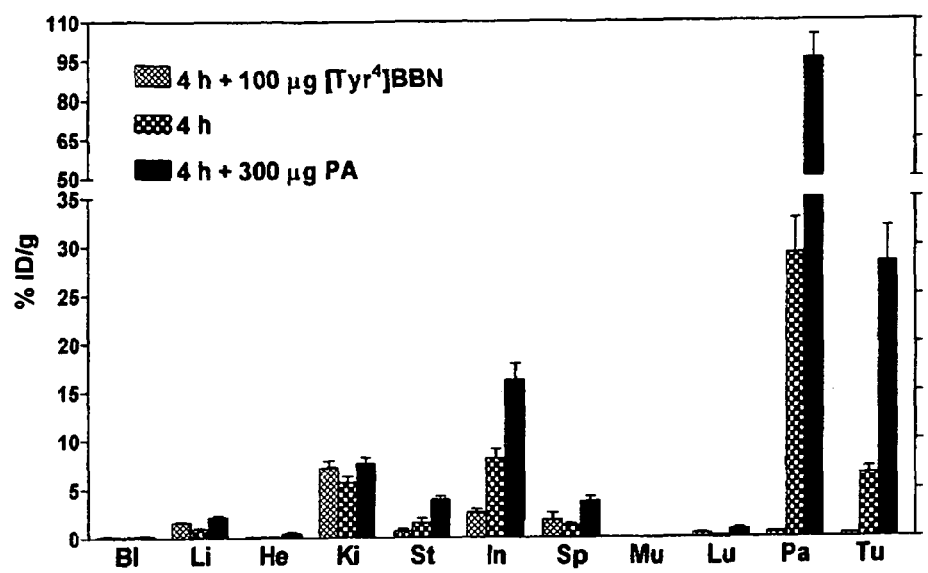
Figure 7B:
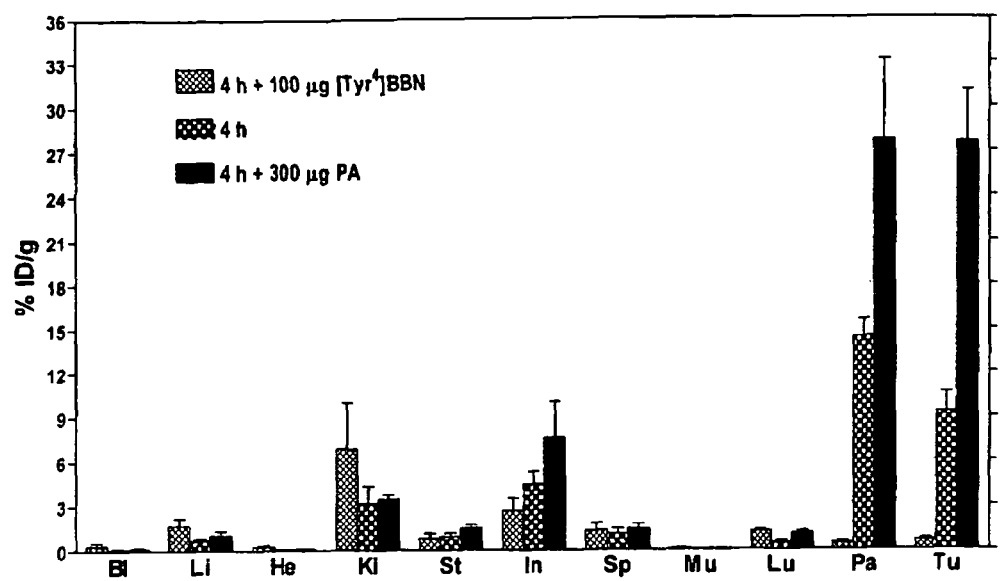

In FIG. 6B and FIG. 7B, the biodistribution of [$^{99m}$Tc]SAR-NC1 and [$^{99m}$Tc]SAR-NC6 in SCID mice bearing human prostate adenocarcinoma PC-3 xenografts (GRPR$^+$) at 4 h respectively, after injection of the radioligand alone or with co-injection of PA (300 µg) are shown. In the PA treated group, animals showed an uptake of 28.34±8.05% ID/g in the experimental tumor vs. 6.51±1.91% ID/g in the non-treated controls for [$^{99m}$Tc]SAR-NC1. In the case of [$^{99m}$Tc]SAR-NC6, the PA treated group, showed a tumor uptake of 27.58±3.47% ID/g vs. 9.22±1.40% ID/g in the non-treated controls.

EXAMPLE 5

Bombesin (BBN)

Targeting of GRPR$^+$ human tumors has been attempted by quite a few bombesin analogs labeled with diagnostic and therapeutic radionuclides (Maina T et al, 2006; Smith C J et al, 2005; Lantry L E et al, 2006; Zhang H et al, 2004; Nock B et al, 2005; Schroeder R P et al, 2011; Ananias H J et al, 2008; Wild D et al, 2011). [$^{99m}$Tc]Demobesin 4 ($^{99m}$Tc—N$_4$-Pro-Gln-Arg-Tyr-Gly-Asn-Gln-Trp-Ala-Val-Gly-His-Leu-Nle-NH$_2$) is a bombesin analog radiolabeled with $^{99m}$Tc via an acyclic chelator coupled to its N-terminal Pro. [$^{99m}$Tc]Demobesin 4 showed promising characteristics in human biopsy specimens and in mice bearing human GRPR$^+$ prostate cancer xenografts while its in vitro stability in mouse plasma was very high. The clinical value of [$^{99m}$Tc]Demobesin 4 as a diagnostic radiotracer is currently under study in prostate cancer patients.

Figures 1, 8A:
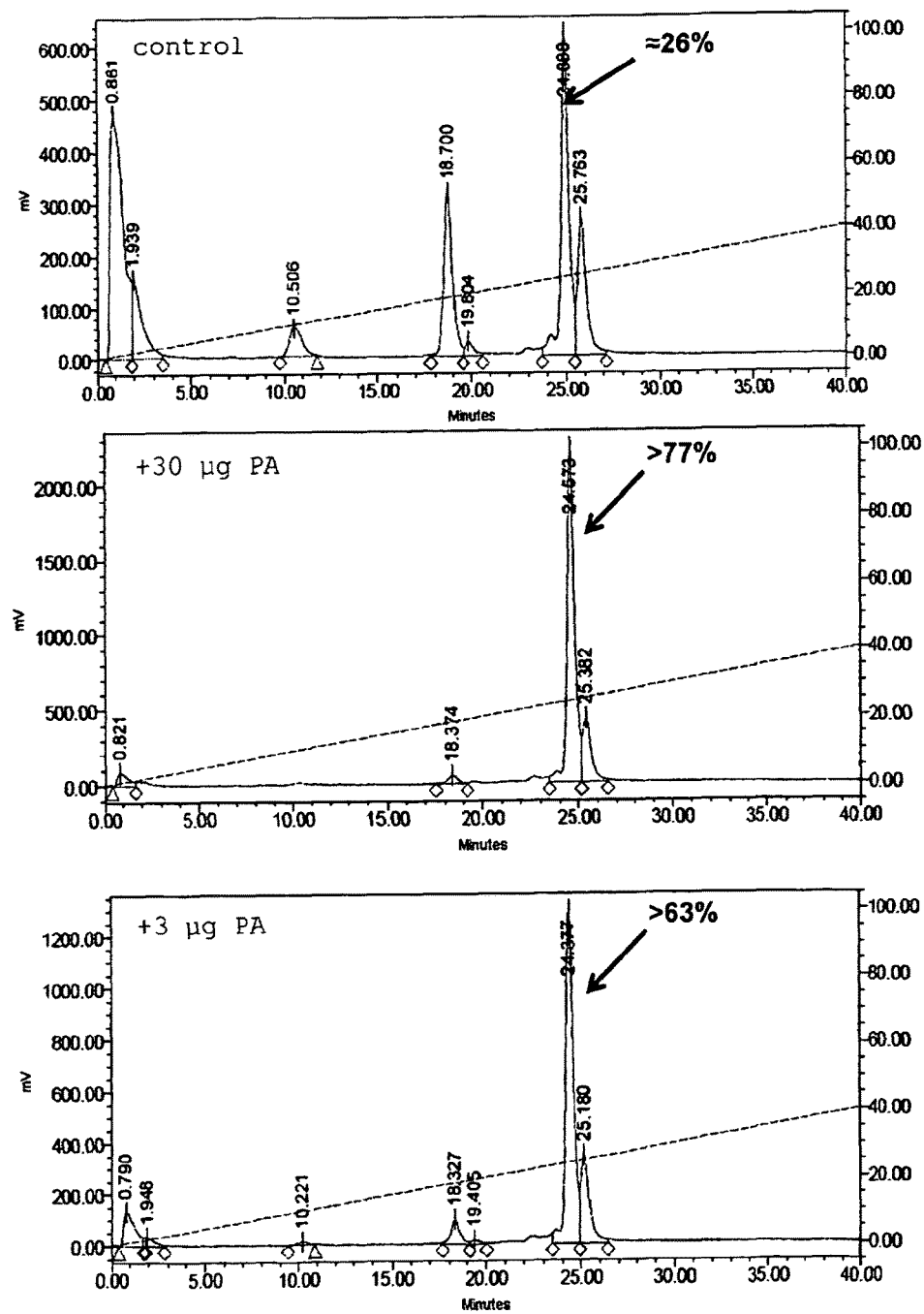
Figures 2, 8A:
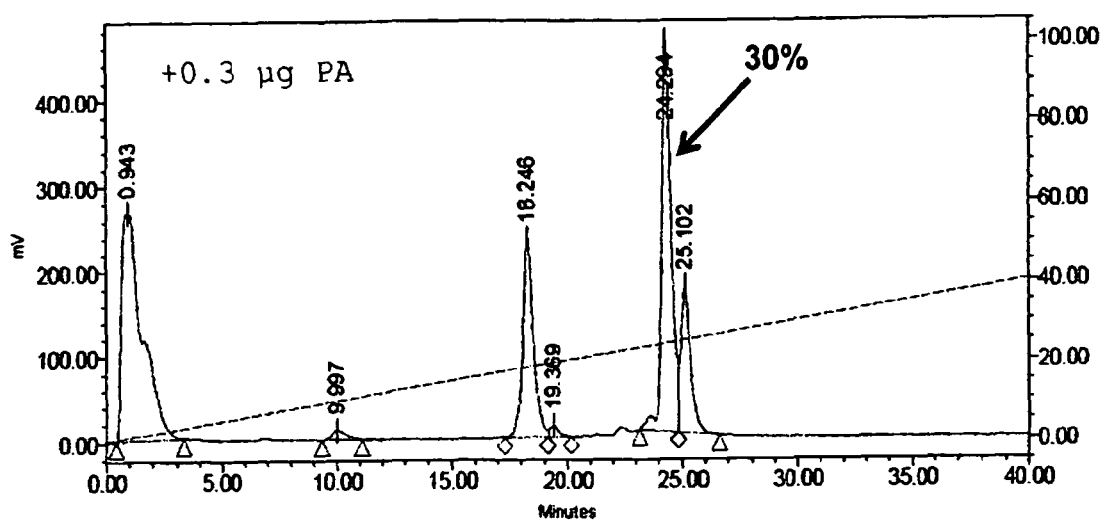

To test the in vivo stability of [$^{99m}$Tc]Demobesin 4 in mice the same protocol as described above was applied. The radiotracer was injected alone or together with decreasing amounts of PA (30, 3 and 0.3 µg) in mice. Results of 5 min ex vivo mouse blood analysis by HPLC are summarized in FIG. 8A. It is very clear to observe that the percentage of [$^{99m}$Tc]Demobesin 4 remaining intact by PA treatment is raised from 26% (control) to >77%, >63% and 30%, respectively.

Figure 8B:
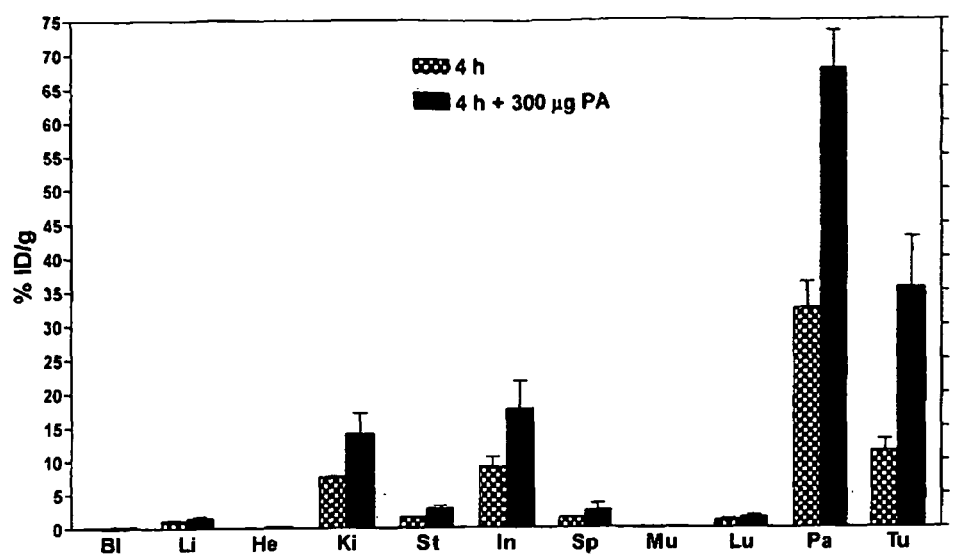

This effect can be elegantly exploited to enhance tumor accumulation, and thereby diagnostic sensitivity, of [$^{99m}$Tc]Demobesin 4, as shown in FIG. 8B, whereby the biodistribution of [$^{99m}$Tc]Demobesin 4 in SCID mice bearing PC-3 xenografts is presented at 4 h after injection of the radioligand alone or with PA (300 µg) It is interesting to note, that in the PA treated group, animals showed a tumor uptake of 35.50±7.50% ID/g vs. 11.26±1.81% ID/g in the non-treated controls.

Figure 9A:
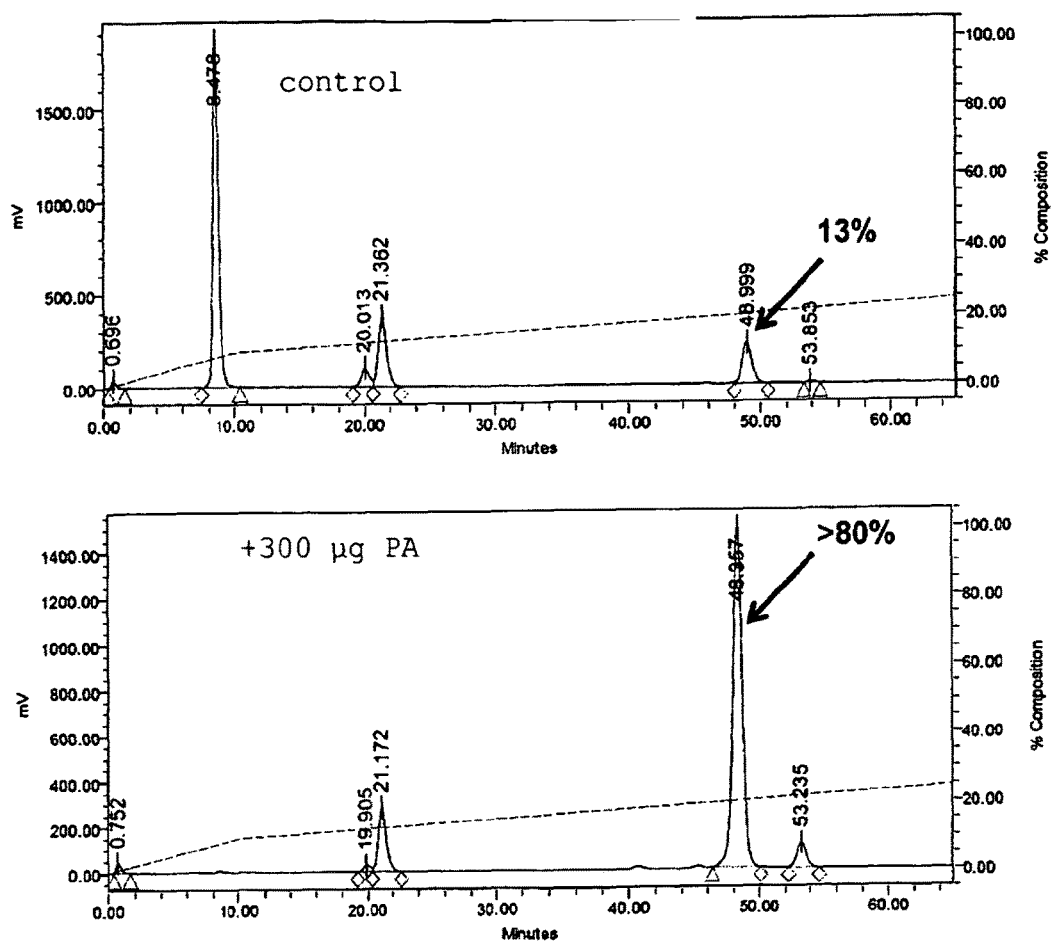

In a second example illustrated in FIG. 9A, [$^{111}$In]Pan-Sarbesin 1 ([($^{111}$In-DOTA-PEG$_2$-DTyr-Gln-Trp-Ala-Val-βAla-His-Phe-Nle-NH$_2$) an $^{111}$In-labeled DOTA-derivatized BBN analog with affinity to all human BBN-receptors (GRPR, NMBR and BB$_3$R) was injected in Swiss albino mice either alone or or with PA (300 μg) and blood was collected 5 min thereafter following the previously described protocol. The respective radiochromatograms (radioligand alone—upper panel) or with PA (300 μg-lower panel) show that the percentage of parent peptide remaining intact by PA treatment is raised from 13% to 80%.

Figure 9B:
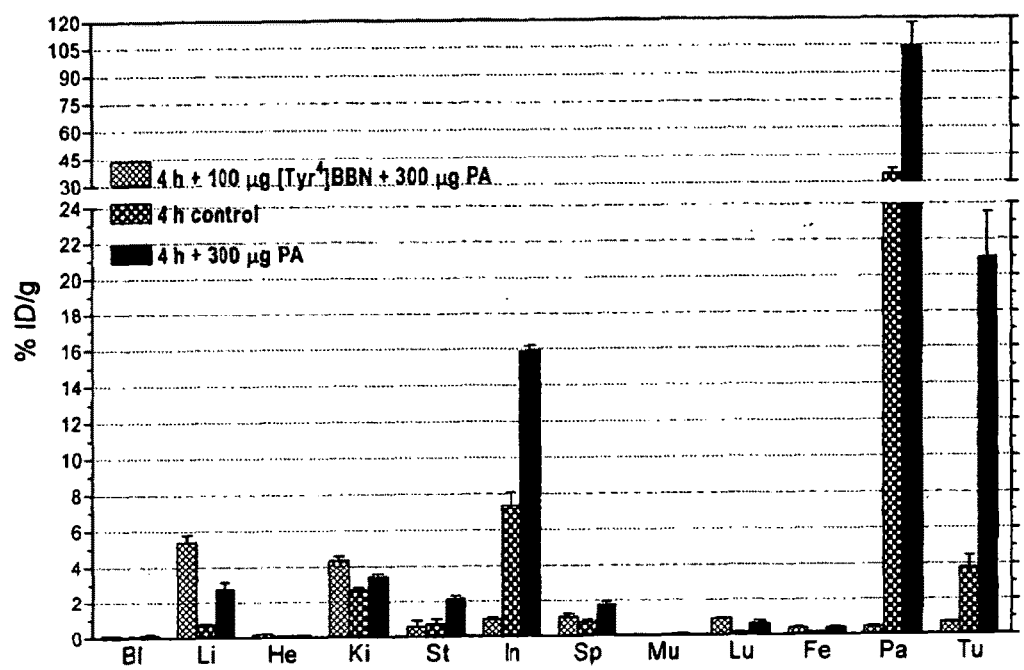

Translation of this effect in enhancement of tumor uptake is quite prominent as can be seen in FIG. 9B, including biodistribution of [$^{111}$In]PanSarbesin 1 in SCID mice bearing PC-3 xenografts (GRPR$^+$) at 4 h pi (control) or with coinjection of PA (300 μg) or with co-injection of excess [Tyr$^4$]BBN (100 μg) in addition to PA (300 μg) along with the radioligand. In the PA treated group, animals showed an uptake of 20.96±2.58% ID/g in the experimental tumor vs. 3.75±0.73% ID/g in the non-treated controls. It is interesting to note that with co-injection of the blocker and PA tumor values were minimal (0.69±0.03% ID/g) showing that PA provoked a GRPR-mediated increase in tumor uptake.

EXAMPLE 6

GRPR-Antagonists

While GRPR-agonists (and in general peptide receptor agonists) have been originally preferred for GRPR targeting of human tumors due to their internalization capacity in cancer cells, increasing evidence reveals superior characteristics of radiolabeled GRPR-antagonists (Nock B et al, 2003; Cescato R et al, 2008; Mansi R et al, 2009; Abd-Elgaliel W R et al, 2008). Given that antagonists do not elicit undesirable adverse reactions after binding to the GRPR they are much better tolerated after iv injection in humans than agonists. In addition, they seem to clear much more rapidly from background tissues, even from the strongly GRPR$^+$ pancreas. This quality often leads to high tumor-to-background ratios after injection of radiolabeled GRPR-antagonists thereby favoring high contrast tumor imaging and high therapeutic efficacy.

Antagonists are synthetic compounds and in general expected to show higher metabolic stability than agonists. The inventors therefore decided to test the in vivo stability of [$^{99m}$Tc]Demobesin 1 ([($^{99m}$Tc—N$_4$)(p-aminobenzyl-diglycolic acid)-[DPhe$^6$,LeuNHEt$^{13}$]BBN(6-13), the first radiolabeled antagonist shown to display superior pharmacokinetics as compared to similarly modified agonists. [$^{99m}$Tc]Demobesin 1 has shown high in vitro stability in mouse plasma, but by analysis of ex vivo blood 5 min pi the percentage of intact peptide was 60-65% (FIGS. 10A-1 and 10A-2).

Figures 1, 10A:
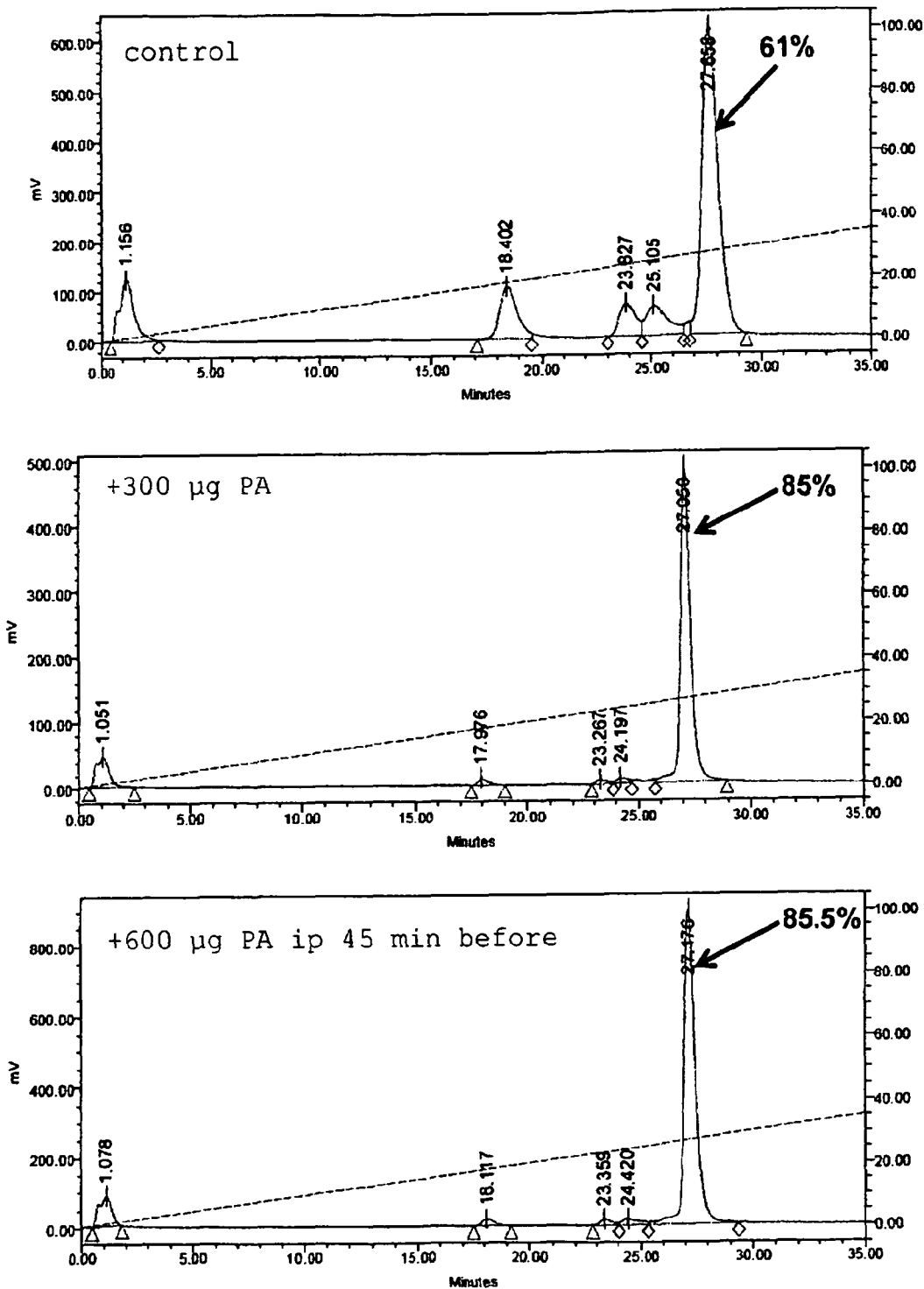
Figures 2, 10A:
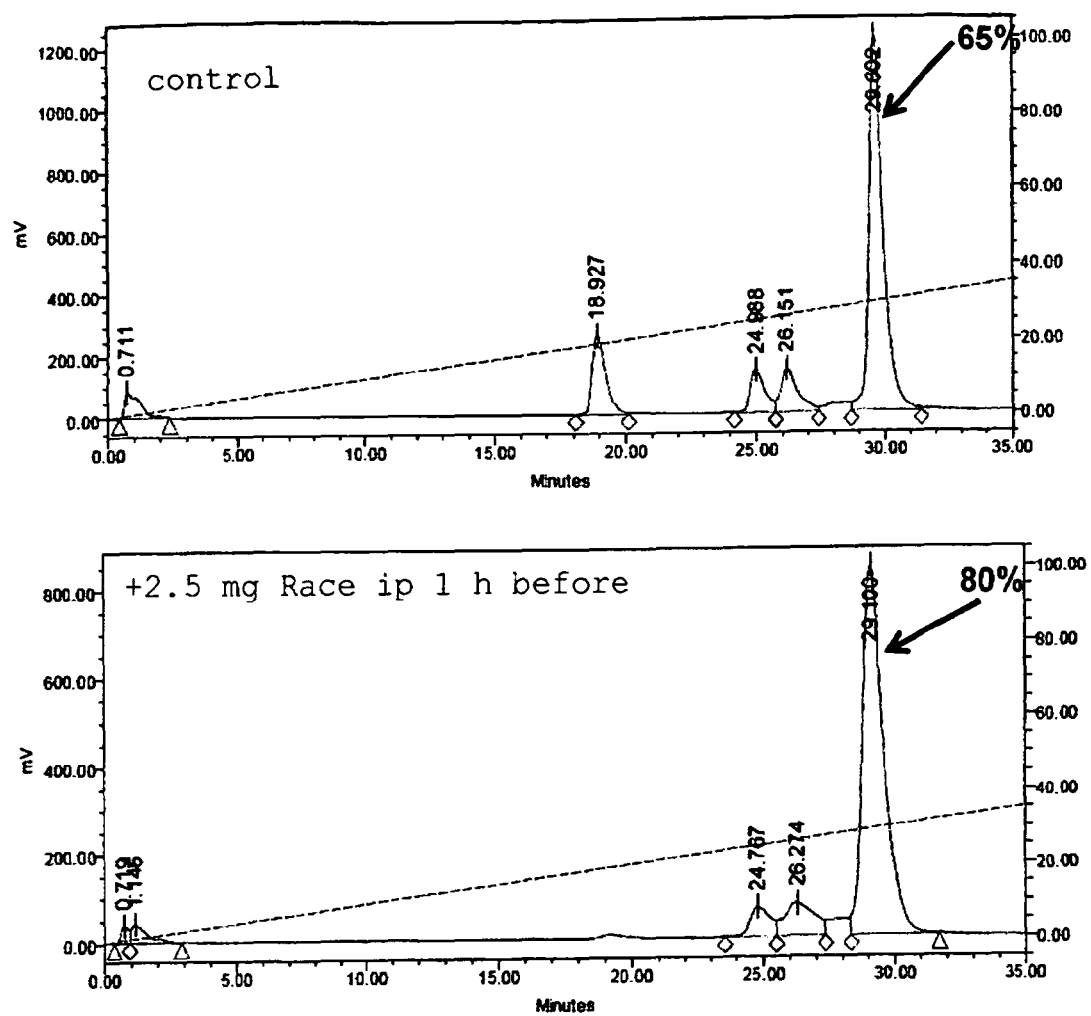

Nevertheless, co-injection of 300 μg PA increased this percentage to >85% and the same increase was observed when 600 μg PA were ip administered 45 min prior to radioligand injection (FIG. 10A). By ip injection of 2.5 mg race 1 h before injection of [$^{99m}$Tc]Demobesin 1 the inventors observed again the same increase in the percentage of parent peptide (FIG. 10A-2).

Figure 10B:
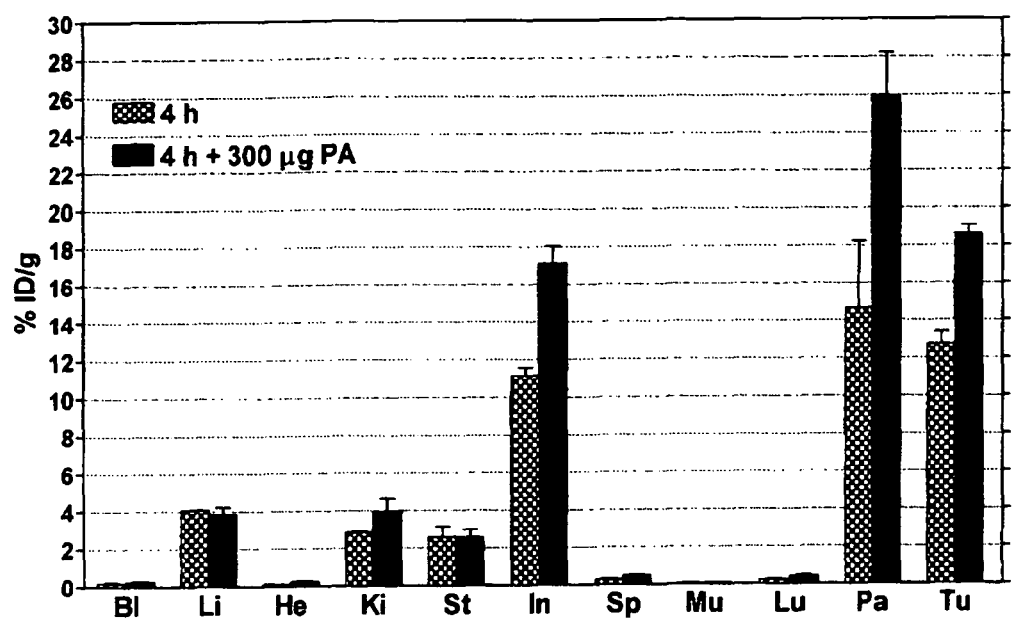

The effect of PA-induced stabilization of [$^{99m}$Tc]Demobesin 1 on tumor uptake is illustrated in FIG. 10B, showing the biodistribution at 4 h pi after injection of [$^{99m}$Tc]Demobesin 1 in SCID mice bearing human PC-3 xenografts (GRPR$^+$) (control), or with PA (300 μg). In the PA treated group, animals showed an uptake of 18.59±0.95% ID/g in the experimental tumor vs. 12.73±0.93% ID/g in the non-treated controls.

Figure 11A:
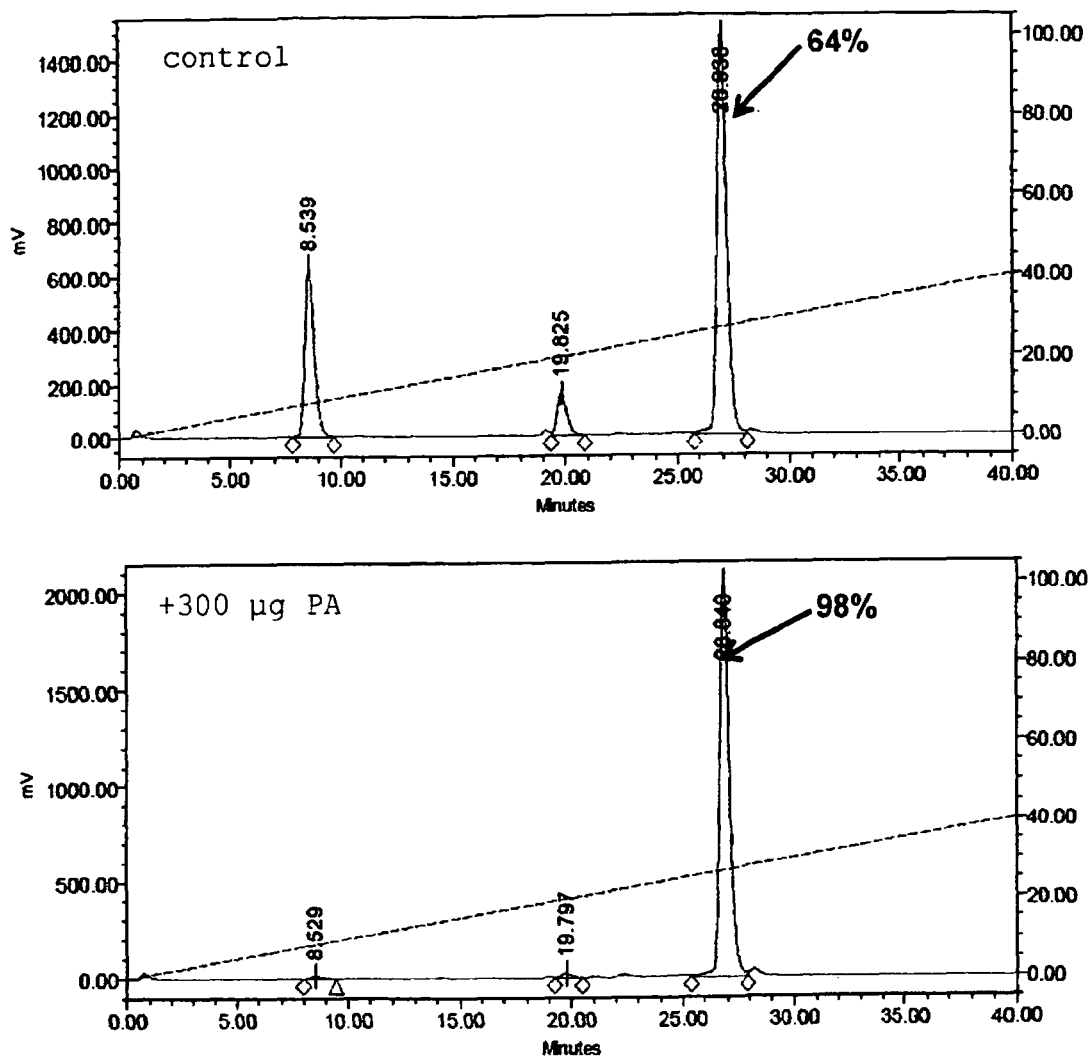

Another characteristic example of the metabolic radioligand stabilization induced by PA is shown in FIG. 11A. The recently synthesized radiotracer [$^{111}$In]JMV4168 ([$^{111}$In] DOTA-βAla-βAla-JMV594, [$^{111}$In]DOTA-βAla-βAla-DPhe-Gln-Trp-Ala-Val-Gly-His-Sta-Leu-NH$_2$) based on the potent GRPR-antagonist JMV594 (Tokita K et al, 2001) was injected in Swiss albino mice alone or together with PA and blood collected after 5 min by HPLC, was analyzed as previously detailed.

[$^{111}$In]JMV4168 showed higher stability (64%) than GRPR-agonists, such as [$^{99m}$Tc]SAR-NCs (30-35%), or [$^{99m}$Tc]Demobesin 4 (26%), and comparable to the GRPR-antagonist [$^{99m}$Tc]Demobesin 1 (61-65%), it clearly profited by PA treatment with 98% remaining stable.

Figure 11B:
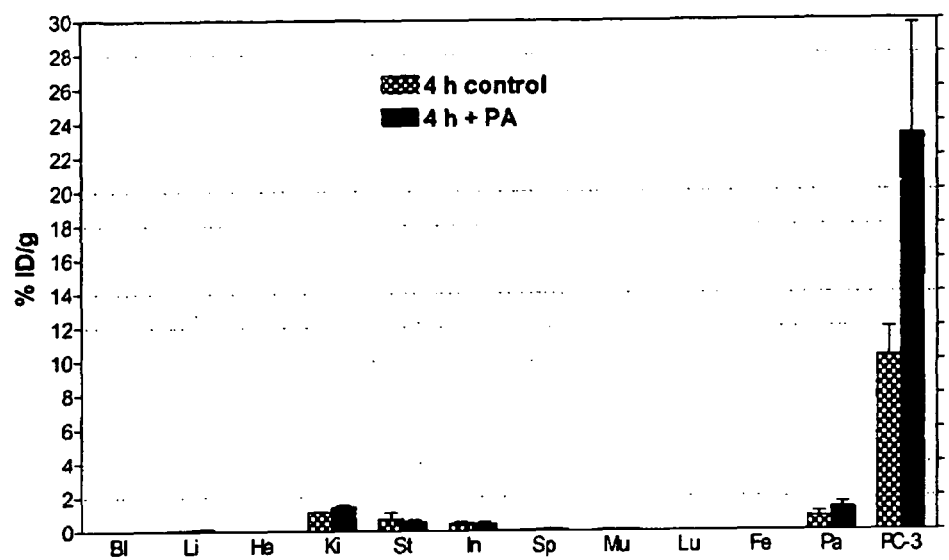

This in vivo prolongation of half-life translated into higher tumor uptake in mice bearing GRPR$^+$ PC-3 xenografts. As shown in FIG. 11B, tumor values raised from 10.22±2.40% ID/g in the non-treated controls to 23.31±11.07% ID/g in the PA-receiving mice. Of great interest is the fact, that pancreas uptake remained very low.

Figure 11C:
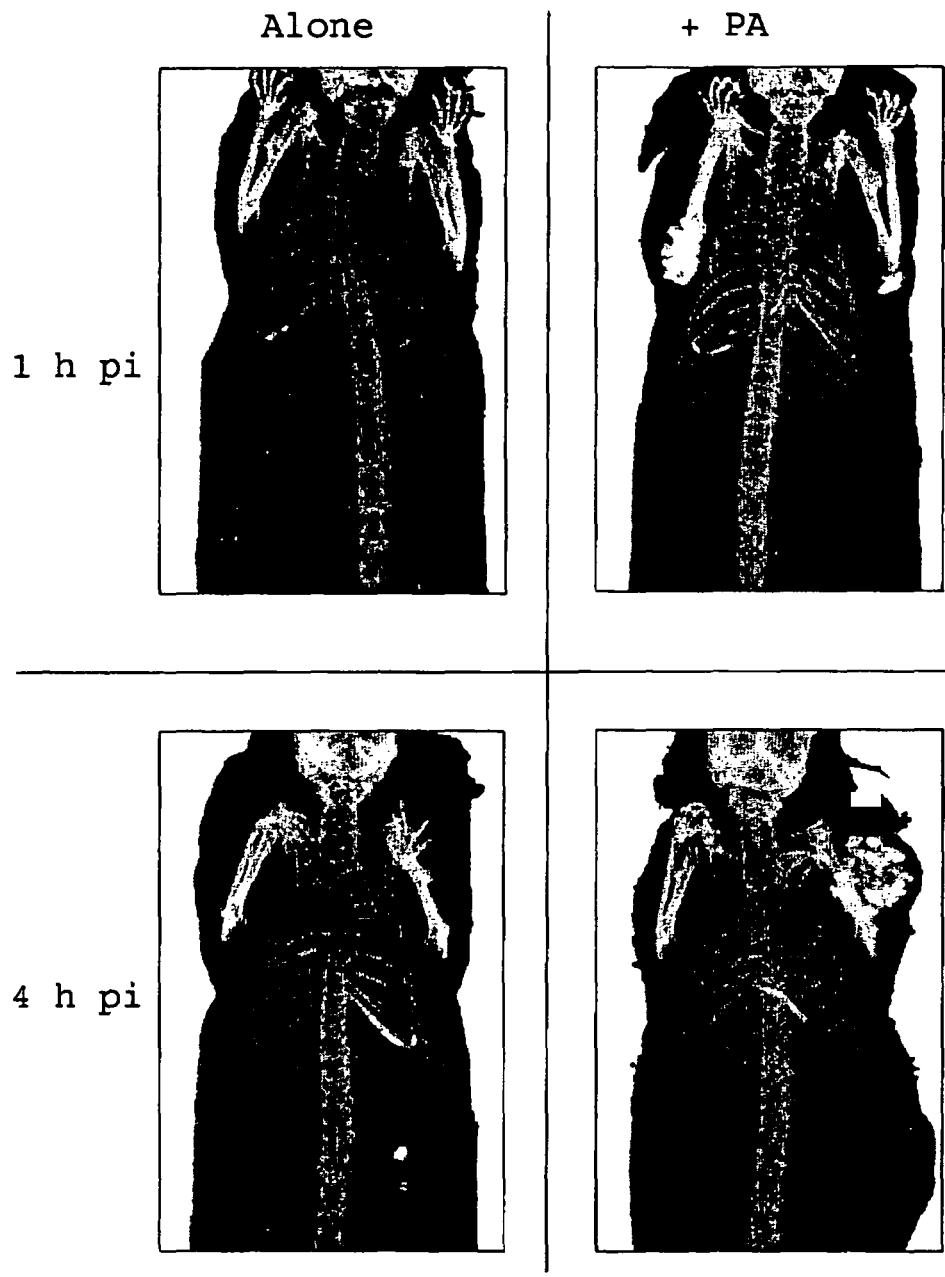

In FIG. 11C, the effect of PA co-injection with [$^{111}$In] JMV4168 on the delineation of an hGRPR$^+$ implanted tumor in a SPECT/CT image was observed. The hGRPR$^+$ PC295 tumors on the shoulder(s) are excellently delineated in the PA-treated animals, whereas in the non-treated controls the uptake is significantly poorer. Furthermore, no evidence of pancreatic uptake is shown in any of the images, in agreement with the results of the respective biodistribution in hGRPR$^+$ PC-3 tumor bearing mice.

This finding has dosimetric implications in the treatment of GRPR$^+$ tumors with radiolabeled GRPR-antagonists. In fact, it is a very powerful modality to selectively enhance uptake on tumor lesions but not to GRPR-expressing tissues like the pancreas, thus sparing them from harmful radiation doses. Since the local enzymatic degradation differs between pancreas and tumor it is possible according to the invention to selectively stabilize radioligands in the tumor and peritumoral milieu only.

EXAMPLE 7

Alternative Peptides

Additional groups of radiopeptides with relevance for nuclear medicine applications have been studied for their in vivo stability. Radiopeptides were injected in the tail vein of healthy mice, either alone, or with a NEP inhibitor (PA—300 μg), or with a NEP (PA—300 μg) and an ACE (Lis—300 μg) inhibitor mixture; alternatively, another NEP inhibitor prodrug (race—2.5 mg) was ip injected in the animals ≈45 min prior to radioligand injection. Blood was collected 5 min afterwards, and analyzed by RP-HPLC after suitable preparation, as previously described.

Figure 12:
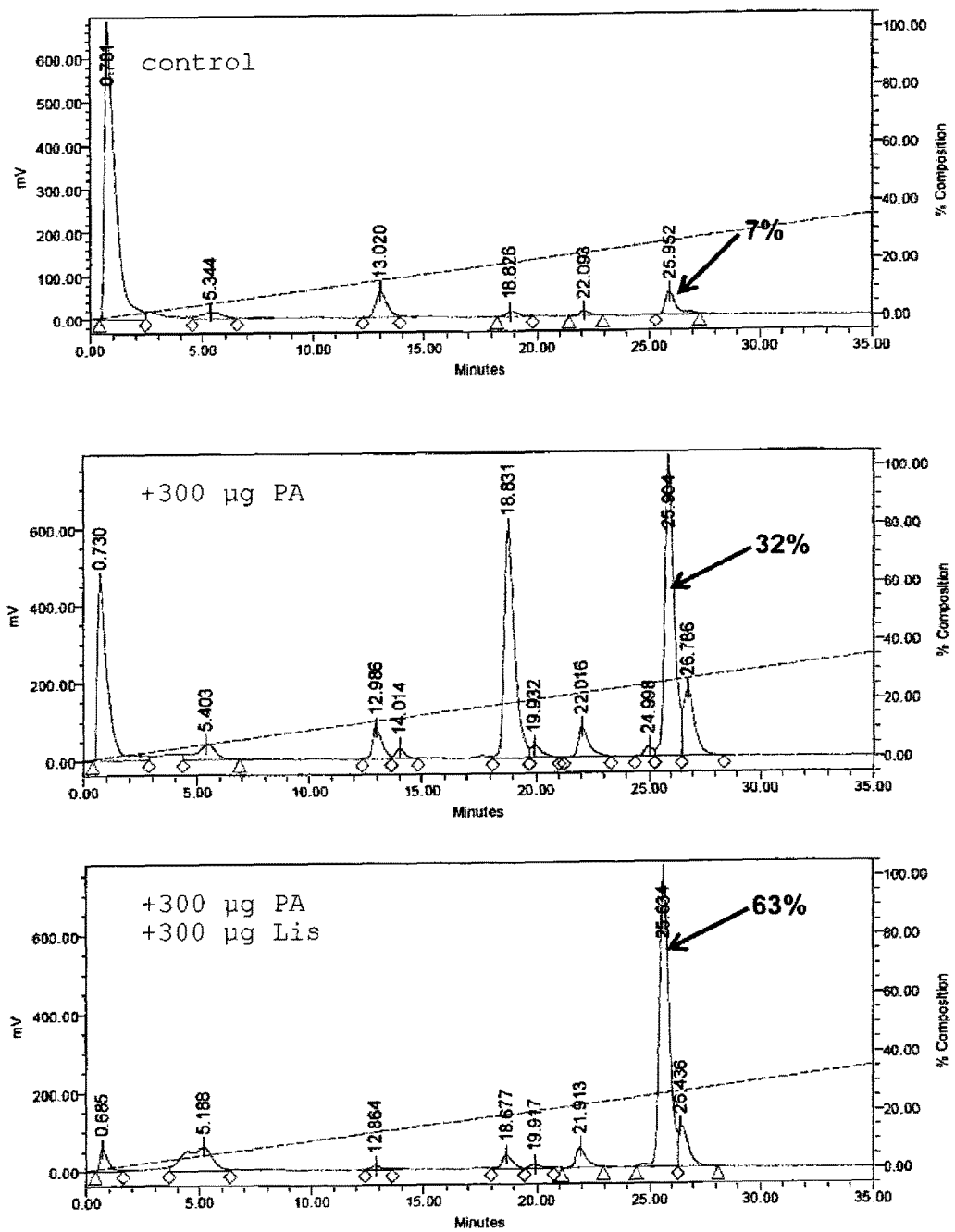

Peptides are Grouped on the Following Catergories:

Substance P analogs: SP-1 is the non-modified SP sequence with DOTA coupled to its N-terminus. The in vivo catabolism of [111In]SP-1 (FIG. 12—upper panel) is extremely fast with only 7% surviving in this period. By co-injection of PA (300 μg) this percentage raises to 32% (FIG. 12—middle panel), while by co-injection of the NEP and ACE inhibitor cocktail (300 μg PA+300 μg Lis) the percentage roses to above 60% (FIG. 12—lower panel), implying the combined role of NEP and ACE in the catabolism of [111In]SP-1 in vivo.

In SP-2, Met11 is oxidized to the corresponding sulfone, reported for its high affinity to the neurokinin-1 receptor subtype (NK1R). In this case inhibition of NEP by PA-treatment raises the percentage of surviving [111In]SP-2 from 24% (FIG. 13—upper panel) to ≈80% (FIG. 13—upper panel) showing that oxidation of Met11 conveys extra stability, especially against ACE.

In SP-3, an additional modification in the original peptide chain, and specifically Gly9 by Sar9 substitution, further increases in vivo stability, with 51% of [111In]SP-3 surviving in circulation (FIG. 14—upper panel) and this percentage rising to almost 90% by PA-co-injection (FIG. 14—lower panel)

MSH analogs: Two MSH analogs for MSH-receptor (MSHR) targeting are coupled to DOTA at their N-terminus and the stability of the respective 111In-radiopeptides studied, as described above. In FIG. 15 (upper panel) we observe that 52% of [111In]MSH-1 survives in mouse blood stream and by PA-co-injection (lower panel) this percentage rises above 90%. Substitution of Phe7 by DPhe7 substantially increases stability in [111In]MSH-2 to 77% (FIG. 16—upper panel). However, PA-co-injection almost totally stabilizes the analog (97% intact peptide: FIG. 16 (lower panel).

Chemotactic peptide (CTP) analogs to target infection as exemplified by [111In] CTP −1. As shown in FIG. 17 (upper panel), only 2% of the radioligand remains intact 5 min after entry into circulation in healthy mice, whereas by PA-co-injection ≈84% survives.

REFERENCES

Abd-Elgaliel W R, Gallazzi F, Garrison J C, et al. Bioconjugate Chem. 19(10):2040-2048; 2008.
Ananias H J, de Jong I J, Dierckx R A, et al. Curr. Pharm. Des. 14(28):3033-3047; 2008.
Cescato R, Maina T, Nock B, et al. J. Nucl. Med. 49(2): 318-326; 2008.
De Visser M, Janssen P J J, Srinivasan A, et al. Eur. J. Nucl. Med. Mol. Imaging 30:1134-1139; 2003.
Gabriel M, Decristoforo C, Woll E, et al. Cancer Biother. Radiopharm. 2011 (in press)
Lantry L E, Cappelletti E, Maddalena M E, et al. J. Nucl. Med. 47(7):1144-1152; 2006.
Maes V, García-Garayoa E, Blauenstein P, Tourwé D. J. Med. Chem. 49:1833-1836; 2006.
Maina T, Nikolopoulou A, Stathopoulou E, et al. Eur. J. Nucl. Med. Mol. Imaging 34:1804-1814; 2007.
Maina T, Nock B, Mather S. Cancer Imaging 6:153-157; 2006.
Mansi R, Wang X, Forrer F, et al. Clin. Cancer Res. 15(16):5240-5249; 2009.
Nock B, Nikolopoulou A, Chiotellis E, et al. Eur. J. Nucl. Med. Mol. Imaging 30(2):247-258; 2003.
Nock B A, Nikolopoulou A, Galanis A, et al. J. Med. Chem. 48(1):100-110; 2005.
Schroeder R P, van Weerden W M, Krenning E P, et al. Eur. J. Nucl. Med. Mol. Imaging 2011—ahead of print
Smith C J, Volkert W A, Hoffman T J. Nucl. Med. Biol. 32(7):733-740; 2005.
Wild D, Frischknecht M, Zhang H, et al. Cancer Res. 71(3):1009-1018; 2011.
Zhang H, Chen J, Waldherr C, et al. Cancer Res. 64(18): 6707-6715; 2004.

The invention claimed is:

1. A composition comprising a radiolabeled biodegradable peptide analog and a neutral endopeptidase (NEP) inhibitor, wherein the radiolabeled biodegradable peptide analog is ($^{111}$In-DOTA)-MG11.

2. The composition of claim 1, wherein the neutral endopeptidase (NEP) inhibitor comprises phosphoramidon or racecadotril.

3. The composition according to claim 1, wherein the composition further comprises an angiotensin-converting enzyme (ACE) inhibitor.

4. The composition according to claim 3, wherein the ACE inhibitor is lisinopril.

5. The composition according to claim 2, wherein the composition further comprises an angiotensin-converting enzyme (ACE) inhibitor.

6. The composition according to claim 5, wherein the ACE inhibitor is lisinopril.

* * * * *